(12) United States Patent
Jamali

(10) Patent No.: US 12,279,778 B2
(45) Date of Patent: Apr. 22, 2025

(54) BONE CUTTING GUIDE SYSTEM FOR OSTEOCHONDRAL TRANSPLANTATION

(71) Applicant: Amir A. Jamali, Oakland, CA (US)

(72) Inventor: Amir A. Jamali, Oakland, CA (US)

( * ) Notice: Subject to any disclaimer, the term of this patent is extended or adjusted under 35 U.S.C. 154(b) by 695 days.

(21) Appl. No.: 17/249,386

(22) Filed: Mar. 1, 2021

(65) Prior Publication Data

US 2021/0322027 A1 Oct. 21, 2021

Related U.S. Application Data

(60) Division of application No. 16/136,111, filed on Sep. 19, 2018, now Pat. No. 10,939,921, which is a continuation-in-part of application No. 14/673,636, filed on Mar. 30, 2015, now Pat. No. 10,105,146.

(60) Provisional application No. 61/972,376, filed on Mar. 30, 2014.

(51) Int. Cl.
*A61B 17/15* (2006.01)
*A61B 17/16* (2006.01)
*A61B 17/17* (2006.01)

(52) U.S. Cl.
CPC ............ *A61B 17/15* (2013.01); *A61B 17/155* (2013.01); *A61B 17/1635* (2013.01); *A61B 17/1746* (2013.01); *A61B 17/1764* (2013.01)

(58) Field of Classification Search
CPC .............. A61B 17/166; A61B 17/1746; A61B 17/15–158
See application file for complete search history.

(56) References Cited

U.S. PATENT DOCUMENTS

| | | | |
|---|---|---|---|
| 5,116,165 A * | 5/1992 | Salyer | A61B 17/1666 407/54 |
| 5,976,148 A * | 11/1999 | Charpenet | A61F 2/34 606/100 |
| 8,241,292 B2 | 8/2012 | Collazo | |
| 2011/0130763 A1* | 6/2011 | Aux Epaules | A61F 2/4609 606/91 |
| 2012/0209276 A1 | 8/2012 | Schuster | |
| 2013/0325016 A1 | 12/2013 | Sordelet et al. | |
| 2014/0243834 A1 | 8/2014 | Chaney et al. | |
| 2014/0249535 A1* | 9/2014 | McCarthy | A61F 2/4684 606/91 |

\* cited by examiner

*Primary Examiner* — Zade Coley
(74) *Attorney, Agent, or Firm* — Andrew F. Young, Esq.; NOLTE LACKENBACH SIEGEL

(57) ABSTRACT

A bone cutting guide for preparing both donor and recipient bone, including one or more articular referencing platforms contoured to a bony surface to be prepared, fixation structure to secure the articular referencing platforms on an articular surface, cutting slots spaced apart from the articular referencing platforms at predetermined distances configured to allow the passage of a saw blade in such a way to remove a bone segment either from an allograft donor or from a graft recipient in such a way that both the removed donor and recipient grafts are of the same exact dimensions, whereby when the allograft is placed in the recipient site of the patient's joint, it completely restores the articular surface to the desired level with healthy articular cartilage from the donor.

7 Claims, 37 Drawing Sheets

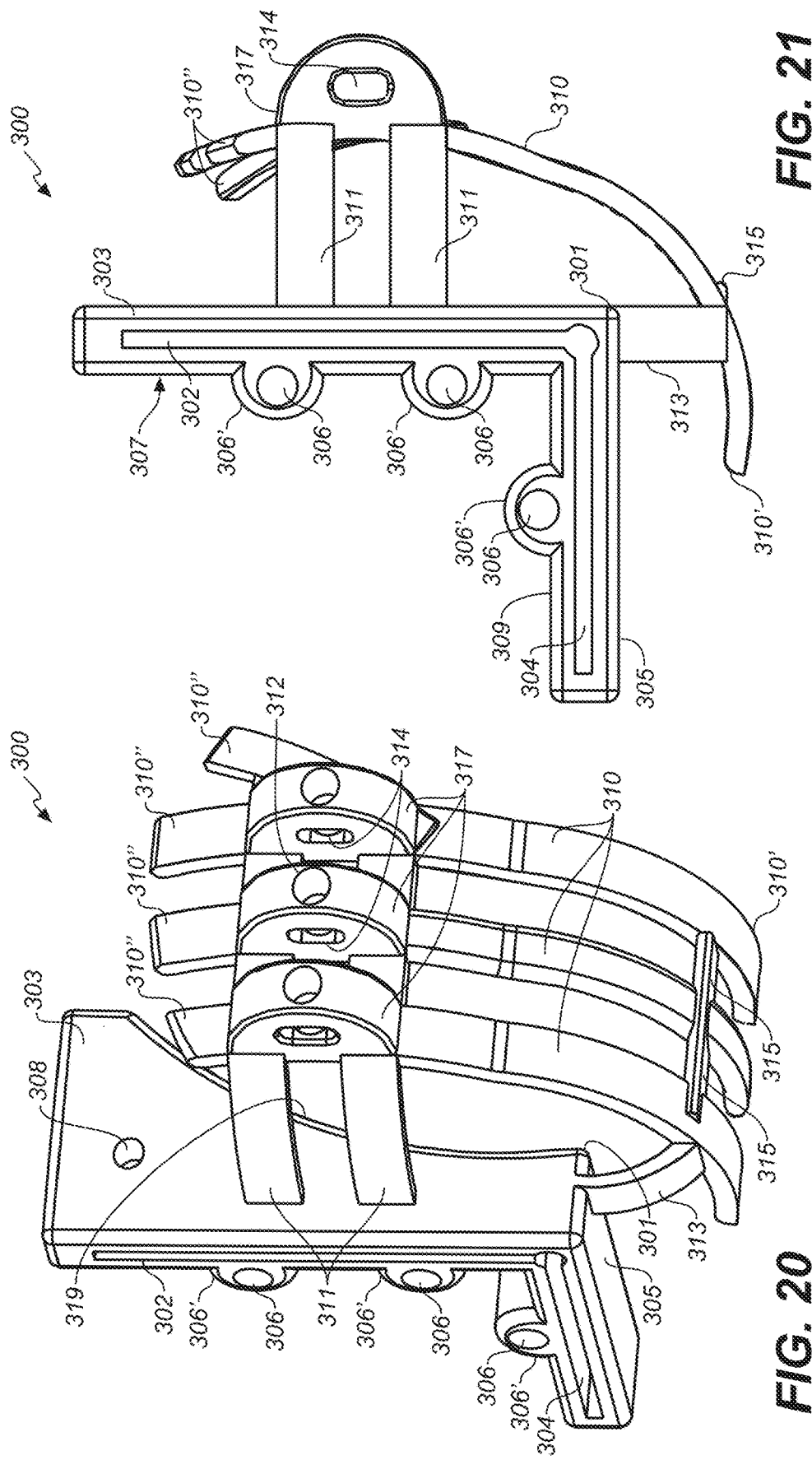

BONE CUTTING GUIDE SYSTEM FOR OSTEOCHONDRAL TRANSPLANTATION

CROSS REFERENCES TO RELATED APPLICATIONS

The present application is a divisional application of Ser. No. 16/136,111, filed Sep. 19, 2018, which is a continuation-in-part of U.S. patent application Ser. No. 14/673,636 (Pat. App. Publ. No. 2015-0272594-A1), filed Mar. 30, 2015, which is incorporated in its entirety by reference herein, and which in turn claims the benefit of the priority date of U.S. Provisional Patent Application Ser. No. 61/972,376, filed Mar. 30, 2014, which application is also incorporated in its entirety by reference herein.

STATEMENT REGARDING FEDERALLY SPONSORED RESEARCH OR DEVELOPMENT

Not applicable.

THE NAMES OR PARTIES TO A JOINT RESEARCH AGREEMENT

Not applicable.

INCORPORATION BY REFERENCE OF MATERIAL SUBMITTED ON A COMPACT DISC

Not applicable.

SEQUENCE LISTING

Not applicable.

BACKGROUND OF THE INVENTION

Field of the Invention

The present invention relates generally to orthopedic medical devices and methods, and more particularly to methods and apparatus for bone transplantation, and more particularly still to devices and techniques for preparing and transplanting osteochondral segments in bone using an angular cutting device attached to the surface of the articular cartilage and thus referencing corresponding bone surfaces on both the donor and recipient sites.

Background Discussion

Current osteochondral allograft technology provides an unsatisfactory solution to the problem of preparing large osteochondral allografts. The state of the art is limited to the use either of hand instruments, such as saws and burrs or, alternatively, large coring devices. When faced with a large bone defect, for instance one involving the entire condyle, the orthopedic surgeon must use multiple interlocking cylindrical cores to resurface the large surface area. This can be problematic because of the increased graft tissue necessary for an interlocking technique. For example, in order to resurface one femoral condyle, a surgeon might require the donor allograft to include an entire distal femur with both condyles. The cost of such a large graft can be prohibitive to the performance of this type of surgery. Total joint replacement is a surgical option with a long history of clinical use. However, it is associated with serious complications such as loosening, wear, and persistent pain. The durability of total joint replacement is limited in young, active patients. Currently, there is no adequate mechanism for the transplantation of large osteochondral allografts of the hip, knee, or ankle. Improved instrumentation will facilitate improvements in patient outcomes from these types of surgeries.

BRIEF SUMMARY OF THE INVENTION

The inventive device and method facilitates the precise preparation of both the donor and recipient bone in such a way that a large bone segment can be fit at the exact position and orientation of the preinjury tissue and in direct contact with the patient's own native bone thus restoring the articular surface and thus the smooth function of a joint.

In embodiments the key elements of the device are the articular referencing platforms and device pins. The articular referencing platforms rest on the articular surface. In such embodiments of the current invention, the articular referencing platforms are contoured to the bony surface to be prepared. Within this cutting device, there are cutting slots provided at a predetermined distance away from the articular referencing platforms and thus the articular surface of the joint. These cutting slots allow the passage of a saw blade in such a way to remove the bone segment either from the donor graft or from the recipient in such a way that both the removed donor and recipient grafts are of the same exact dimensions. When the graft is placed in the recipient site of the patient's joint, it completely restores the articular surface to the desired level with healthy articular cartilage from the donor. In order to allow for the completion of any additional angular cuts, additional guides and fixation devices are placed on the cutting guide based on the specific needs of the procedure. In one of disclosed embodiments of the invention, for the preparation of a femoral condyle, a separate attachable tower is mounted on the original cutting jig. This attachable tower facilitates the precise cutting of the diseased femoral condyle or femoral condyle graft away from the associated femoral trochlea. For example, once the femoral condylar graft has been applied into its recipient site it achieves initial stabilization to the bone through direct contact over a large bony surface and through friction between the posterior condyle, the distal condyle, and the anterior wall of the trochlea. Additional fixation is achieved with standard screws and plates as needed and as commonly practiced in the art of orthopedic surgery. The above described guides can be used alone or in combination to allow transplantation of either one or both femoral condyles. Furthermore, the guides can be utilized with a separate attached trochlear tower which rests on the two femoral condylar guides and allows for recovery of the trochlea as a single entity. Alternatively, by utilizing both condylar guides and the trochlear tower, the entire surface of the human distal femur can be transplanted. Thus the disclosed invention allows transplantation of either one or both femoral condyles independently, one femoral condyle with the femoral trochlea, the femoral trochlea in isolation, or potentially, the entire surface of the distal femur if indicated.

In the current document, we have expanded on the previous disclosures of devices for the preparation of the knee and disclosed additional iterations of the device, notably for the preparation of the human acetabulum or hip socket, femoral condyles, and femoral trochlea of the knee. For the human acetabulum, the majority of cases of hip arthritis start in the superior weight-bearing portion of the acetabulum. As a result, in certain cases the full resurfacing of the hip socket is not necessary. However, there is a need for a reliable method to resurface just the weight-bearing portion of the acetabulum. The current disclosure provides two methods for performing limited resurfacing of the hip socket. The first of these is a modular acetabular cutting tool that precisely contacts the articular surface of the acetabulum. This referencing guide is disposed with two cutting slots or channels, oriented radially to the base of the guide, and a set height of reference from the hemispherical articular surface of the acetabulum. The cutting slots are disposed in a radial orientation to the base of the guide and each contains a cutting channel. The radially oriented cutting slots allow the surgeon to cut orthogonally to the acetabular cartilage surface and references at an angle of between 30 and 150 degrees to one another. An axial cutting tool is then placed on the flat surface formed at the top of the radially oriented cutting slots. This axial cutting tool is disposed with a central cutting slot for placement of a saw in order to separate the bone previously cut through the radial cutting channels of the guide. This process allows for the complete separation of the acetabular graft of set thickness and essentially parallel to the articular surface at a set distance away from the cartilage. The triangular segment is removed from the donor and recipient using either reciprocating or oscillating bone saws or a cutting burr system through the three cutting slots described above (two radial and one axial).

The second described cutting tool for the acetabulum, described here as the monoblock acetabular cutting guide is a unitary (one-piece) cutting block which references off the articular surface but contains the three described cutting channels within its body. It provides the advantage of easier application to the surface but the disadvantage of less visualization of the entire surface of the acetabulum.

In another embodiment, the inventive bone cutting guide is adapted for the preparation of the femoral trochlea. It shares commonalities with other embodiments based on referencing the articular surface of the joint to be resurfaced. Its unique characteristics are the use of multiple referencing pins extending through the articular side of the guide. These again serve to orient the guide at the desired distance from the articular surface of the joint to obtain a graft of set thickness and orientation. The unique qualities of this device are that it provides for the harvest of the trochlea with a triangular chevron shape that leads to increased stability after transplantation, limits the overall thickness of the graft, which is important for graft survival, and by adjustment of the reference pins allows for conversion of a malformed femoral trochlea to a trochlea with normal morphology and smooth transition to the remaining portion of the knee at the distal femur.

From the foregoing, it will be seen that in its most essential aspect, the inventive medical device is a bone cutting guide for preparing both donor and recipient bone which includes: one or more articular referencing platforms contoured to a bony surface to be prepared; fixation structure to secure the articular referencing platforms on an articular surface; cutting slots spaced apart from the articular referencing platforms at predetermined distances configured to allow the passage of a saw blade in such a way to remove a bone segment either from an allograft donor or from a graft recipient in such a way that both the removed donor and recipient grafts are of the same exact dimensions, whereby when the allograft is placed in the recipient site of the patient's joint, it completely restores the articular surface to the desired level with healthy articular cartilage from the donor.

BRIEF DESCRIPTION OF SEVERAL VIEWS OF THE DRAWINGS

The invention will be better understood and objects other than those set forth above will become apparent when consideration is given to the following detailed description thereof. Such description makes reference to the annexed drawings, wherein the orientation of the views corresponds to the anatomical position orientations of the inventive apparatus when installed on an acetabulum (as seen in FIGS. 10-13, and 19, or on a femoral condyle (as seen in FIGS. 28-30), or when installed on a femoral trochlea (as seen in FIGS. 51-54):

FIG. 20 is an inferior right lateral perspective view of the femoral condylar cutting guide of the present invention;

FIG. 21 is right lateral view in elevation thereof;

DETAILED DESCRIPTION OF THE INVENTION

Figure 1:
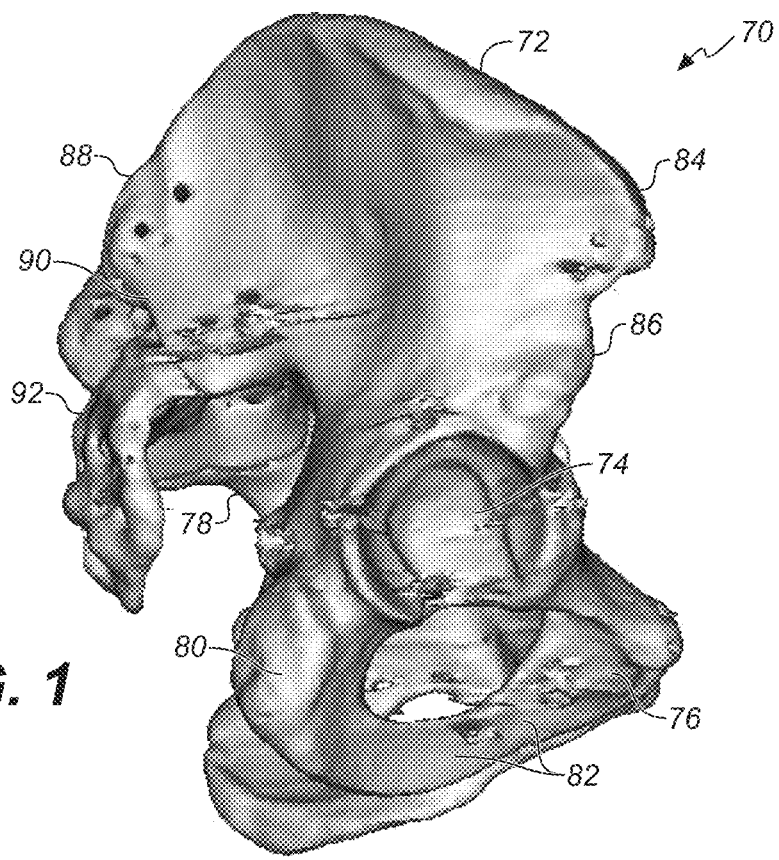
FIG. 1 is a lateral right side view of the human pelvis and sacrum.

Referring first to FIG. 1, there is shown a human pelvis 70, showing the iliac crest 72, the acetabulum 74, the pubis 76, the greater sciatic notch 78, the ischium 80, the ischiopubic ramus, 82, the anterior superior iliac spine 84, the anterior inferior iliac spine 86, the posterior superior iliac spine 88, the posterior inferior iliac spine 90, and the sacrum 92.

As seen first in FIGS. 1-13, in an embodiment 100 the bone cutting guide system of the present invention, the modular acetabular cutting tool, can be adapted for use in acetabular transplantation procedures. When so adapted, the device includes a hemispherical reference guide provided in multiple sizes between 40 and 60 mm in 1 mm increments. In the most general terms, the main cutting tool includes a hemispherical body with two vertical cutting slots or channels radially oriented in relation to the perimeter of a lower rim of the hemispherical guide (thus, substantially perpendicular to the widest perimeter of the hemispherical guide). These two cutting channels can be angled between 30 and 150 degrees from one another, with an ideal angle of 90 degrees. The channels extend to and through two outriggers, which each include a vertically oriented body with a vertically oriented cutting slot aligned with one of the cutting channels or slots in the hemispherical body. At the top of the two vertical cutting towers, a planar (flat) support is established for placement of a second cutting tool, i.e., an axial cutting tool. The axial cutting tool is placed atop the vertical cutting towers. This axial cutting tool is oriented parallel to the widest perimeter of the hemispherical guide. It contains a cutting slot perpendicular in orientation to the vertical cutting extensions and is disposed such that at the outer edge of its cutting slot, a pin hole is established. A metal guide pin is placed in this hole to stabilize the axial cutting tool to the acetabular bone, but also acting as a stop to keep the cutting saw from cutting outside the trajectory of the guide pin. The guide pins are placed in the axial cutting tool such that they are exactly vertical to the two cutting channels of the vertical cutting guide. In this way, once the entire assembly is applied these two cutting guides act as a stop of the saw cuts of the vertical cutting guides as well. The vertical distance from the extension of the horizontal cutting slot to the top of the hemisphere establishes the vertical thickness of the acetabular allograft.

The same technique for retrieval of the graft is used for removal of the diseased acetabular segment. The steps involve applying the hemispherical guide to the acetabulum, pinning the guide in place, placing the axial cutting tool on the modular acetabular cutting tool, applying guide pins to the horizontal guide, cutting through the vertical cutting paths, and cutting through the horizontal cutting paths. Finally, the guide is removed and the bone segment is removed, whether from the donor graft or from the patient's (recipient's) acetabulum.

Figure 2:
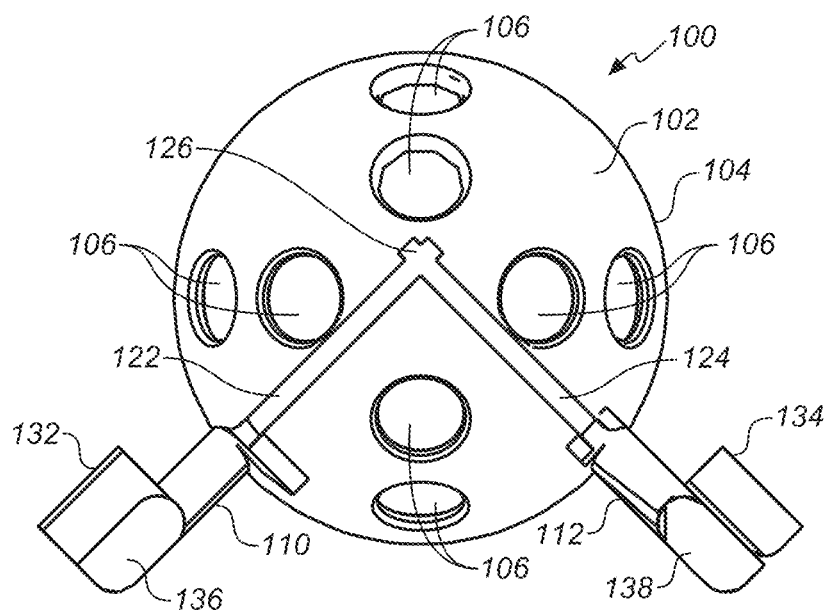
FIG. 2 is a superior (top plan) view of an embodiment of the bone cutting tool of the present invention, shown here as the modular acetabular cutting tool.
Figure 3:
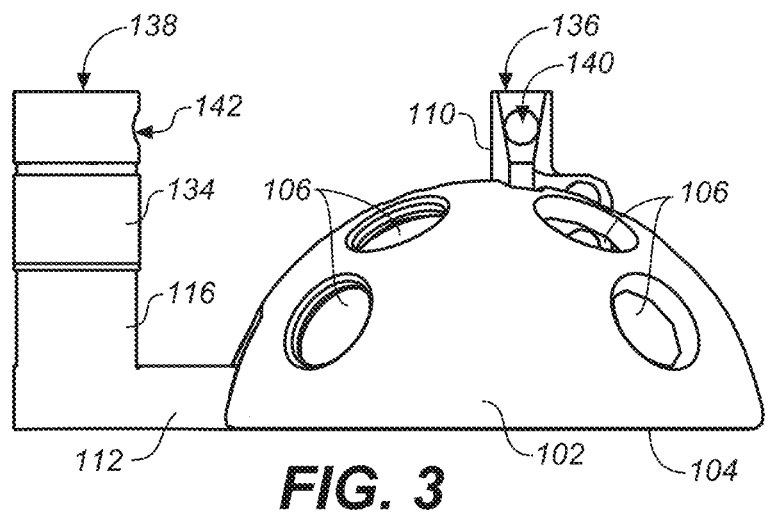
FIG. 3 is a lateral (side) view in elevation of the modular acetabular cutting tool.
Figure 4:
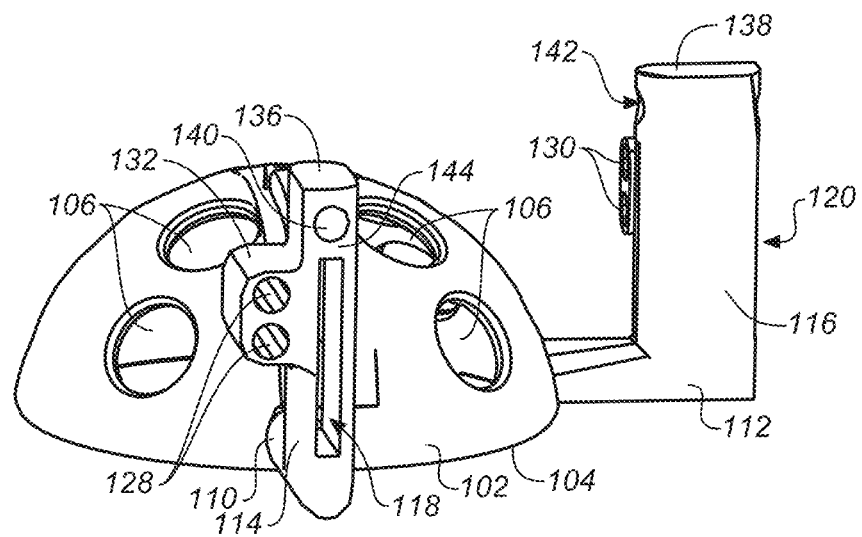
FIG. 4 is an upper perspective view of the modular acetabular cutting tool.

Looking specifically at FIGS. 2-4, there are shown a superior (top plan) view, side view in elevation, and upper perspective view, respectively, of a modular acetabular cutting tool 100 in an embodiment of the bone cutting guide of the present invention. As seen in this view, the modular acetabular cutting tool 100 includes a hemispherical dome 102 with a generally planar bottom edge 104 and a plurality of fenestrations (in this embodiment, circular) 106 through which a surgeon can confirm complete contact between the guide and the acetabular cartilage. Extending radially from the lower portion 108 of the hemispherical dome 100 are two outriggers 110, 112, each having a vertically oriented tower 114, 116, thus giving the outrigger and towers an L-shaped configuration in an embodiment, and each vertical tower in turn having vertically disposed cutting slots or channels 118, 120 that are each aligned with a vertically oriented cutting slot 122, 124, respectively, in the hemispherical dome. The cutting slots 122, 124 converge and cross at the apex 126 of the hemispherical dome and may be radially separated or angled on the dome at any of a number of angles between 30 and 150 degrees, with 90 degrees a preferred angle. A saw is reciprocated through the slots in the cutting towers and cutting slots to obtain a wedge cut through the acetabular roof.

The towers 114, 116 of the outriggers 110, 112, each include a first set of peripheral fixation holes 128, 130, disposed on a small protrusion 132, 134 near the upper end of the slots 118, 120. The fixation holes are used to hold the guide in the desired position adjacent to the acetabular rim. The vertically oriented cutting slots 118, 120 through the hemispherical guide extend through the outriggers. A flat upper surface 136, 138, is established at the top of each outrigger tower for placement of the axial cutting tool. An additional fixation hole 140, 142 is disposed proximate the top of each outrigger tower. These holes have axes parallel to fixation holes 128, 130.

Figure 5:
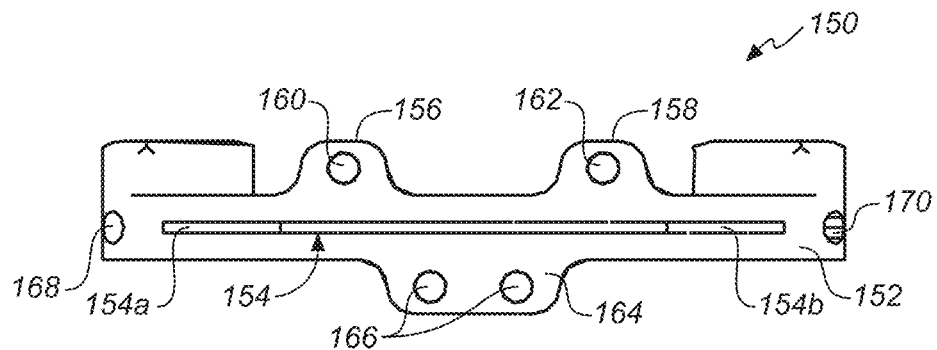
FIG. 5 is an anterior view of the axial cutting tool used in combination with the modular acetabular cutting tool in the bone cutting guide system.
Figure 6:
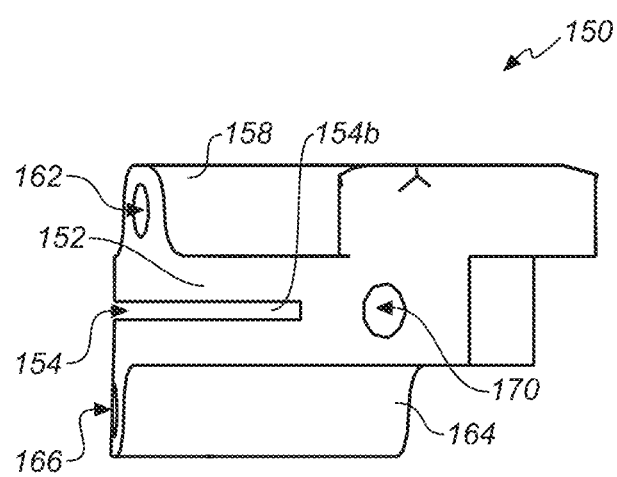
FIG. 6 is a lateral view thereof.
Figure 7:
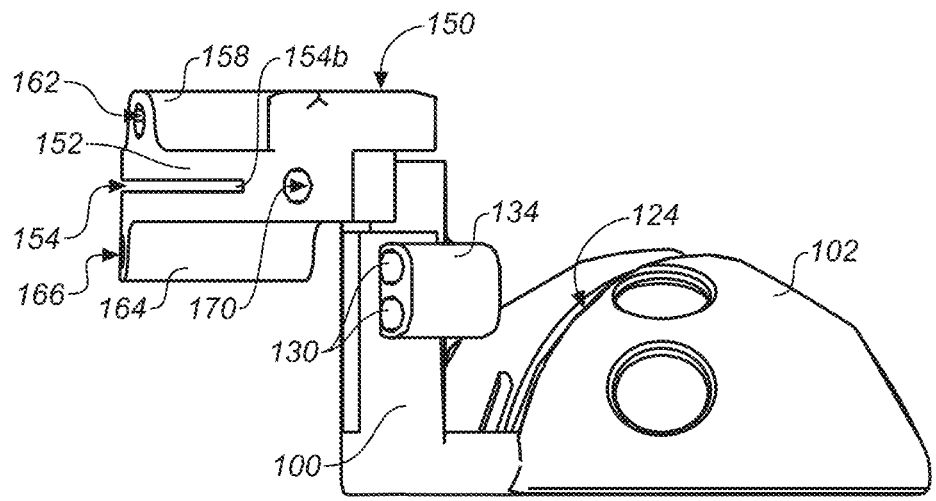
FIG. 7 is a lateral view in elevation of the combined assembly of the modular acetabular cutting tool and the axial cutting tool.
Figure 8:
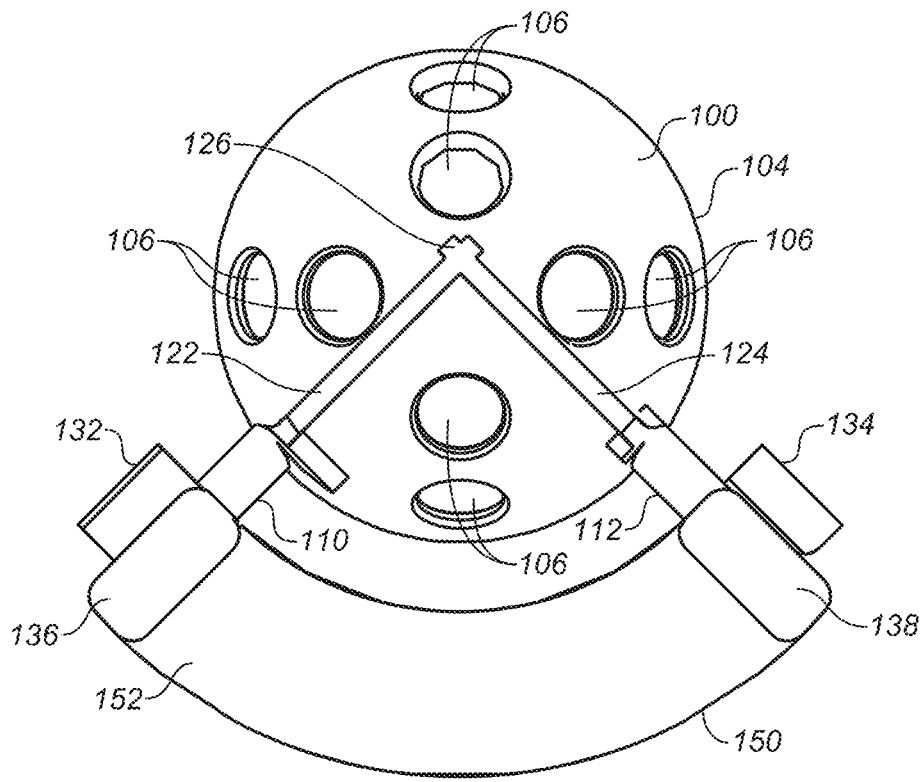
FIG. 8 is a superior view of the combined assembly of the modular acetabular cutting tool and the axial cutting tool.
Figure 9:
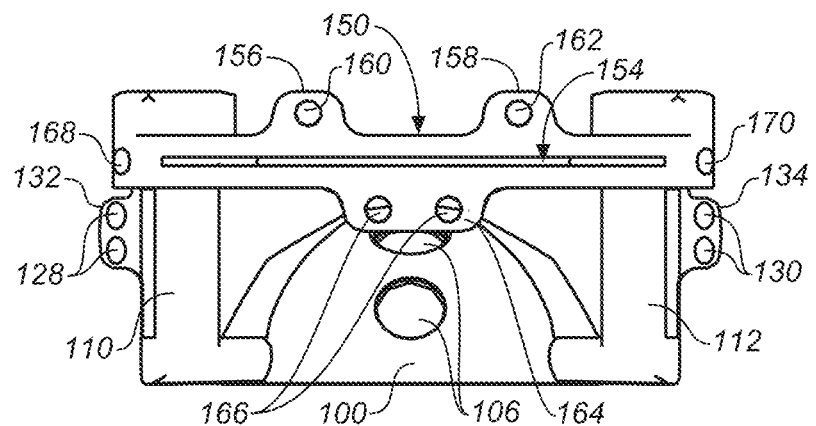
FIG. 9 is an anterior view of the combined assembly of the modular acetabular cutting tool and the axial cutting tool.

FIGS. 5-6 are, respectively, an anterior view and a lateral view of the axial cutting tool 150 used in the cutting guide assembly, while FIGS. 7-9 show how the axial cutting tool is placed on the flat surfaces (136, 138 in FIGS. 2-4) of the cutting towers 110, 112 of the modular acetabular cutting tool 100 to make the combined assembly.

The axial cutting tool includes an arcuate bar 152 as viewed in top plan view (see FIG. 8) and includes a horizontally oriented cutting slot 154. The arcuate bar includes upper bosses 156, 158, each with fixation holes 160, 162, and at least one lower boss 164 with fixation holes 166. Additional fixation holes 168, 170 may be disposed outside the ends 154a, 154b of the horizontally disposed cutting slot 154. When the axial cutting tool is mounted on the flat surfaces 136, 138 of the cutting towers, the fixation holes 140, 142 disposed proximate the top of each outrigger tower is collinear with the additional fixation holes 168, 170 outside the ends of the horizontally disposed cutting slot 154. This serves to firmly affix the axial cutting tool both to the bone and to the modular acetabular cutting tool.

Figure 10:
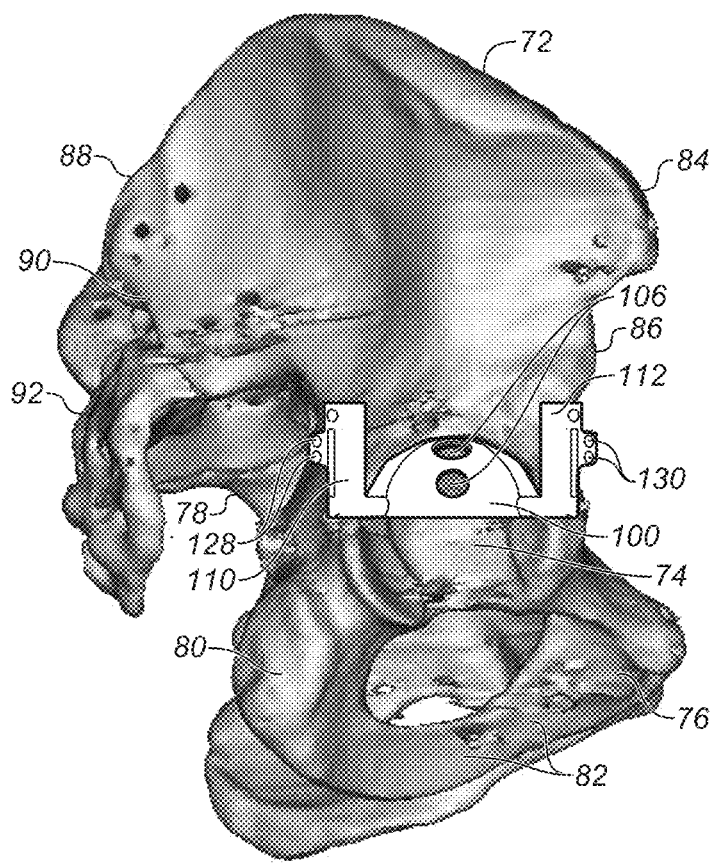
FIG. 10 is a lateral view of the human pelvis showing the iliac crest, the acetabulum, and the sacrum, with the modular acetabular cutting tool placed flush against the surface of the socket.
Figure 11:
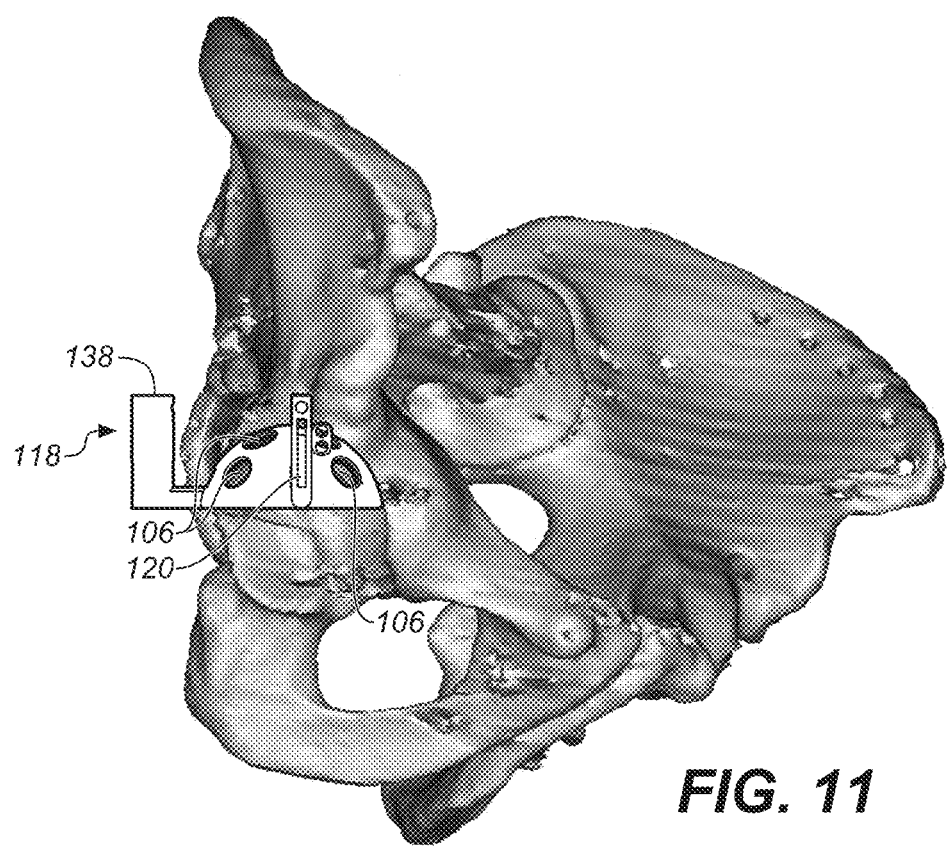
FIG. 11 is a perspective view of the human pelvis showing the iliac crest with the modular acetabular cutting tool placed against the surface of the socket.

FIGS. 10-11 are lateral and perspective views, respectively, of the human pelvis showing the modular acetabular cutting tool 100 placed flush against the surface of the acetabular socket by contact of the fenestrations 106 around the guide with the cartilage of the acetabulum. The outriggers 110, 112 extend outward and upward and contain the peripheral fixation holes 128, 130, for attachment of the guide to the acetabulum. The outriggers extend outward and upward and at FIG. 11 demonstrate the vertically oriented tower cutting slots 118, 120, aligned with the vertically oriented slots 122, 124 in the hemispherical guide to obtain a wedge cut through the acetabular roof.

Figure 12:
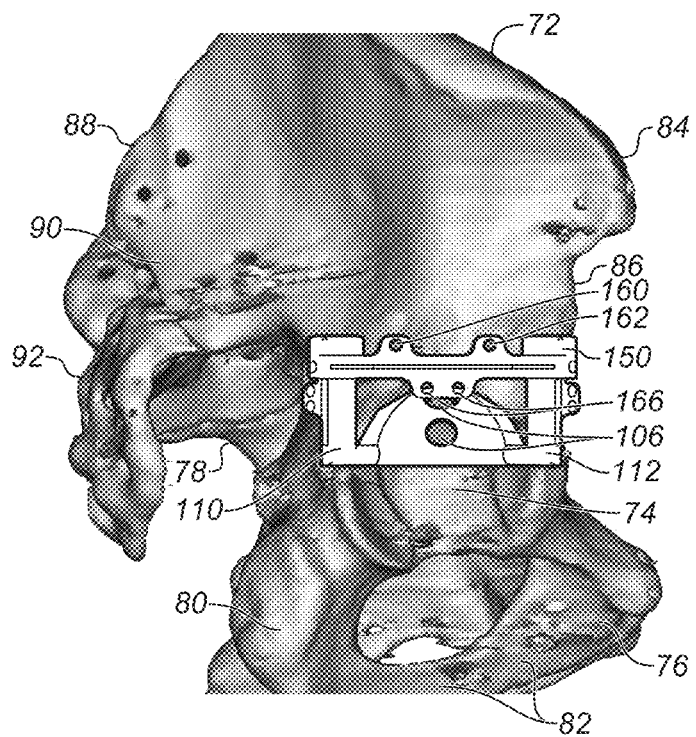
FIG. 12 is a lateral view of the human pelvis showing the iliac crest with the combined assembly of the modular acetabular cutting tool and the axial cutting tool.
Figure 13:
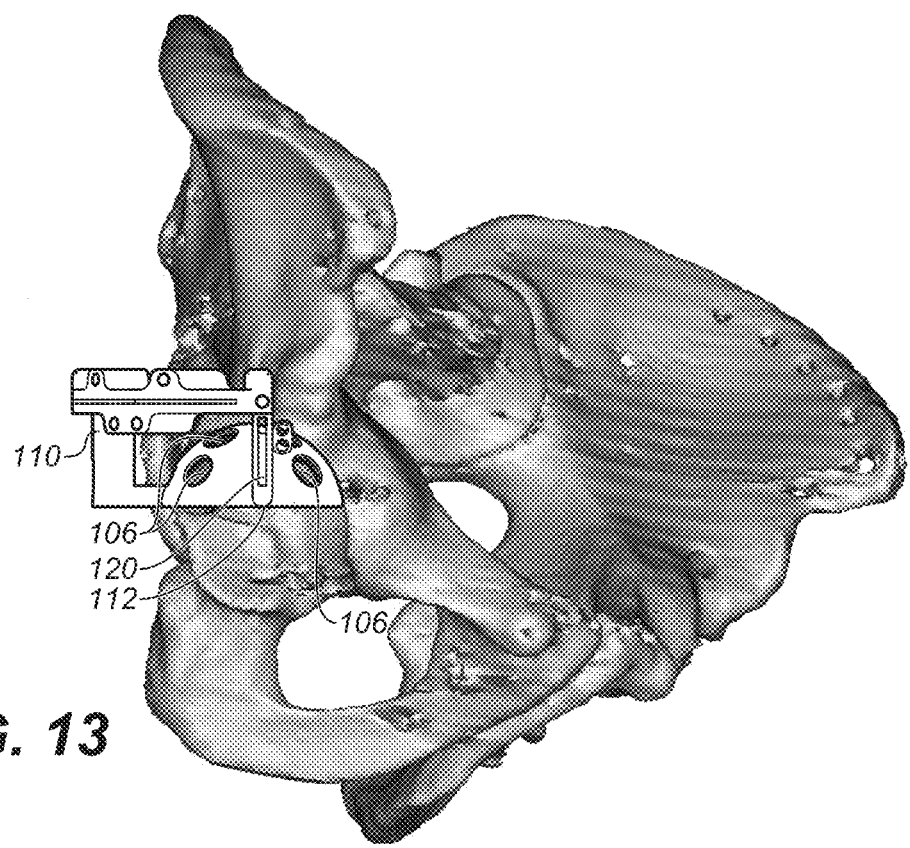
FIG. 13 is a perspective view of the human pelvis showing the iliac crest with the combined assembly of the modular acetabular cutting tool and the axial cutting tool affixed.

FIGS. 12-13 are, respectively, a lateral and a perspective view of the human pelvis showing the combined assembly of the modular acetabular cutting tool 100 and the axial cutting tool 150 with its superior attachment holes 160, 162, and its horizontally disposed cutting slot 154. Again, the modular acetabular cutting tool 100 is placed flush against the surface of the acetabular socket by contact of the fenestrations 106 around the guide with the cartilage of the acetabulum.

In another embodiment 200, the monoblock acetabular cutting guide shown in FIGS. 14-19—this embodiment again adapted for use in acetabular transplant procedures— the device includes a unitary (one-piece) cutting tool with both an axial cutting slot and vertical cutting slots so as to provide cutting guides of the kind described in connection with the embodiment of FIGS. 2-13, and thus a device that facilitates the removal of osteochondral grafts from the acetabulum.

This embodiment 200 of the inventive cutting tool includes a concave surface which approximately matches the edge of the acetabulum and a convex hemispherical central extension that matches the contour of the acetabulum. By resting the vertical portion of this concave complementary surface against the rim of the acetabulum, the guide is set in its position in the horizontal plane. By placing the horizontal portion of this concave surface and its central extension against the rim and the surface of the acetabulum respectively, the guide is set in its position in the vertical plane. The guide is disposed with a multitude of fixation holes on its sides as well as on its superior surface allowing it to be held in a stable position during the preparation and removal of the graft segments.

The guide is disposed with two vertical cutting slots angled between 30 and 150 degrees from one another. The guide is disposed with at least one horizontal guide at its superior surface facilitating the separation of the superior segment of the graft from the donor pelvis.

Figure 14:
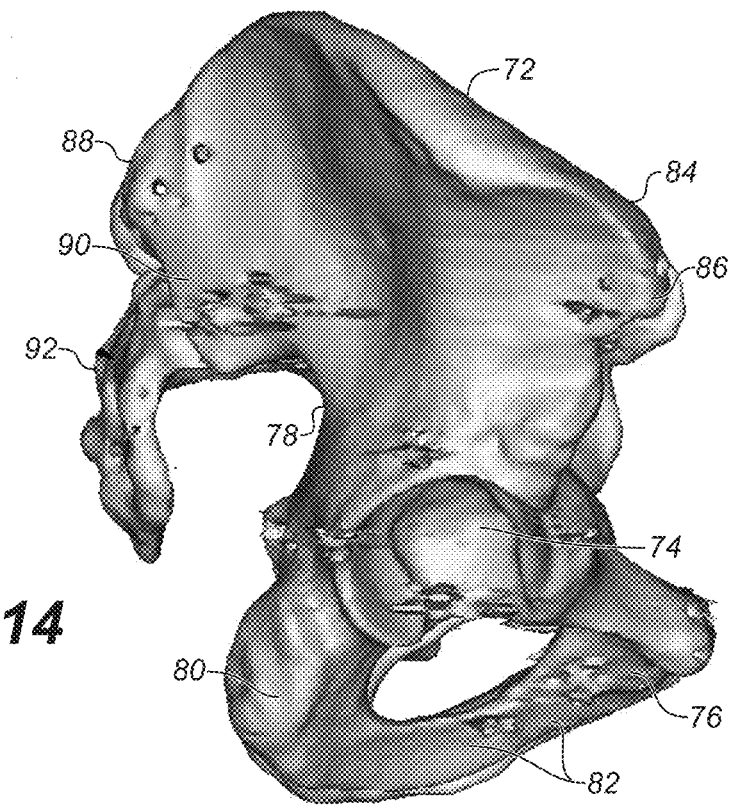
FIG. 14 is a lateral view of the human pelvis showing the iliac crest, the acetabulum, and the sacrum, shown from a viewing angle slightly superior to that of the view of FIG. 1.
Figure 15:
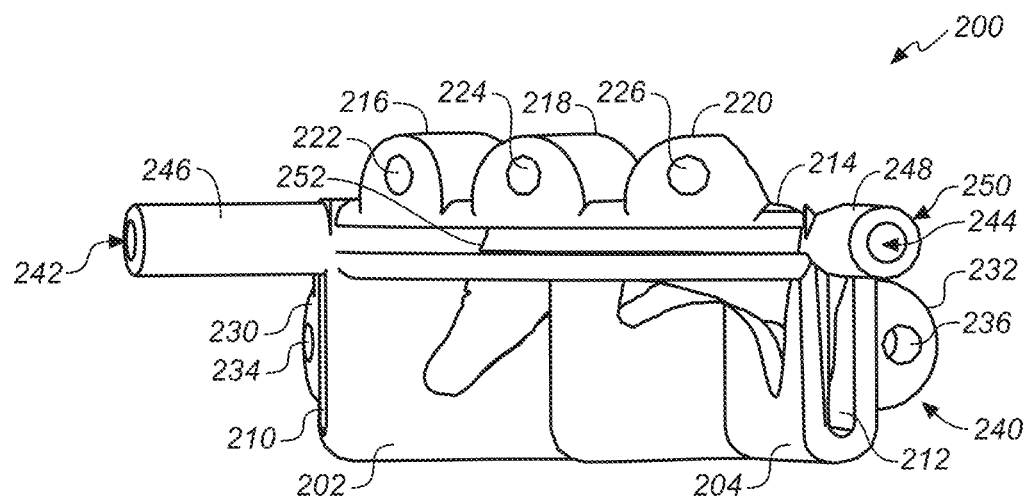
FIG. 15 is an outer perspective view of the monoblock acetabular cutting tool.

FIG. 14 is a lateral view of the human pelvis shown from a viewing angle slightly superior to that of the view of FIG. 1.

FIGS. 15-18 are, respectively, an outer perspective view, a lateral view, an inner perspective view and a superior view of an embodiment 200 of the acetabular cutting tool, the monoblock acetabular cutting guide. In this embodiment, tool includes arms 202, 204, which converge at a vertex 206 and are separated by an angle 208, which may be between 30 and 150 degrees, but which is preferably 90 degrees.

Each arm includes a vertical slot 210, 212 which extends through the arm and functions as a saw blade guide. An arcuate bar 214 extends between and joins the arms and includes upper bosses 216, 218, 220, each having a fixation pin hole 222, 224, 226, respectively. A medial support strut 228 (FIG. 18 only) extends from the vertex 206 to the arcuate bar 214.

Each arm 202, 204 includes a projection 230, 232 shaped to support a peripheral fixation hole 234, 236 at the outer edge of the arm as a raised boss. Additional fixation pin holes 242, 244 are disposed through tubes 246, 248 integral with the guide at the superior aspect 250 of the guide immediately above their respective vertical slots 210, 212. A horizontal cutting slot 252 allows the saw to be placed parallel to the surface of the acetabulum with a set thickness based on the parameters of the guide, i.e., the vertical distance between the concave surface of the guide and the horizontal cutting slot and the vertical distance between the convex surface of the top of the vertex 206. Cutting through sequentially through the vertical cutting slots 210, 212 followed by through the horizontal cutting slot enables complete separation of the acetabular graft from the rest of the acetabulum.

FIG. 19 is a lateral view of the human pelvis and acetabular cutting tool 200 demonstrating the structural and operational elements of the device when installed on an acetabular socket for removal of either a graft or preparation of a graft recipient site.

Referring next to FIGS. 20 through 37, there is shown another embodiment of the bone cutting guide system for osteochondral transplantation of the present invention.

Referring first to FIGS. 20-21, cutting guide 300 is seen to comprise a cutting guide block 301 including a distal portion (in reference to the femoral condyle to which it is applied) 303 and a posterior portion 305 generally normal to the distal portion. A distal cutting slot 302 is disposed through the distal portion 303 of the cutting guide block 301 and a posterior cutting slot 304 is disposed through the posterior portion 305. Fixation holes 306 for the guide are shown on both the distal and posterior portions and are preferably disposed through semi-cylindrical bosses 306 or other structure integral with, respectively, the proximal side 307 of the distal portion and the anterior side 309 of the posterior portion. A fixation through hole 308 is provided in the distal portion for mounting and securing an attachable tower (discussed more fully below). The cutting guide block distal and posterior portions may be generally planar on their exposed surfaces, though such a configuration is not essential to the operability of the assembly.

At least one condylar rail, and preferably a plurality of spaced apart and generally parallel condylar rails 310, is attached to both the distal and posterior portions of the cutting guide block, the former, distal portion with at least one, and preferably two, cross bars 311; and the latter, posterior portion with a single strut 313. A lower cross bar 315 provides structural support proximate the lower ends of the condylar rails and may extend so as to be contiguous with strut 313, or it may be a discrete cross-bar structure.

The condylar rails are configured with a curvature to rest on the distal femoral cartilage contacting this surface intimately as a reference of the spatial location and orientation of the cartilage surface. Along the distal aspect of the guide and disposed on the outer surfaces of the condylar rails are one or more screw guide bosses 317 having screw guide tracks or apertures 314 disposed therethrough, into and through which a screw guide passes and slides, such that the screw guide is disposed generally transversely across and in front of (distally in relation to) the condylar rails. At least one stabilization bolt hole 312, (bolt not shown) is provided through one or more of the screw guide bosses for placement of a bolt to securing and stabilize the screw guide within the screw guide bosses and within the screw guide track 314. The screw guide is slidably adjustable within the screw guide track for precise positioning on the bone.

It will be seen that the condylar rails include curvature that extends so as to provide a lower posterior rail portion 310N and partially 310NN engaging the posterior cartilage surface when in place, and similarly include curvature so as to provide an anterior rail portion 310NN.

It will be recognized that the cutting guide block 301 is configured with curvature 301N on the condyle-engaging side (though the curvature may be either medial or lateral) of the cutting guide block in the condyle capturing region of the condylar rails so as to closely engage the distal femoral condyle when surgically placed.

Figure 22:
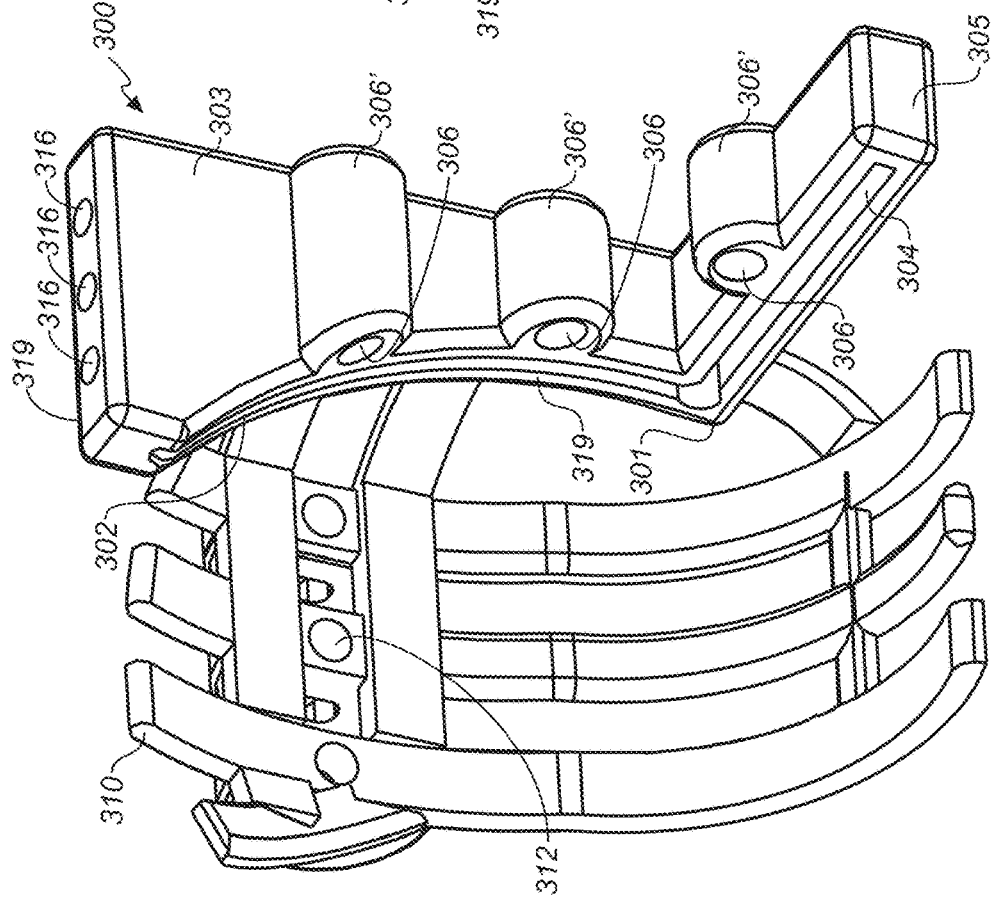
FIG. 22 is a superior and medial perspective view thereof.

Referring next to FIG. 22, which is a posterior lateral perspective view of the cutting guide, there is shown the distal cutting slot 302 in cutting guide block 301. The posterior cutting slot is shown by 304. Fixation holes 306 in the guide are shown and are seen to be through holes. The anterior condylar rail portions 310NN rest on the anterior, distal bone surface to be cut. The screw hole 312 for stabilization of the screw guide is shown. The anterior condylar rail portions 310NN extend so as to provide an anterior rail portion that rests on the anterior femoral condyle. The anterior cylindrical female elements 316 of the cutting guide are shown disposed in the anterior edge 319 of the anterior portion 303 of the cutting guide block 301. This is the docking or attachment site of the attachable tower cutting guide shown in FIGS. 23-25.

Figure 23:
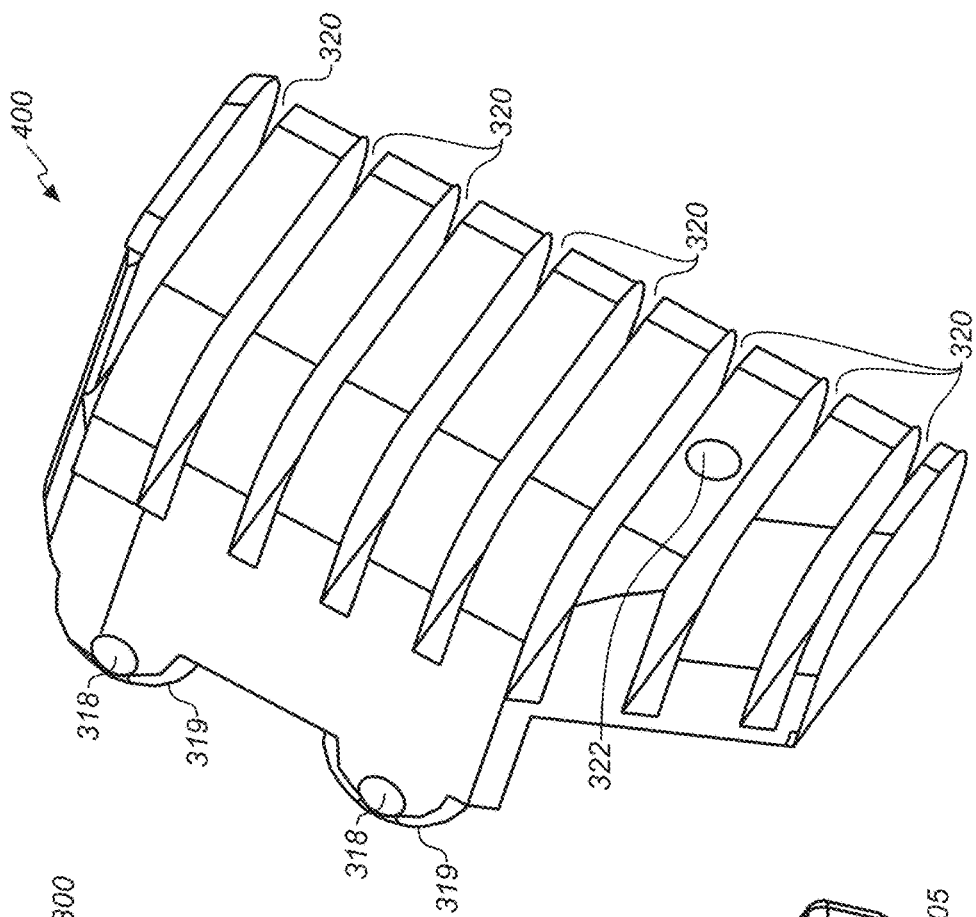
FIG. 23 is an inferior and right lateral perspective view of the attachable tower for the femoral condylar cutting guide of the present invention.

FIG. 23 is a perspective view of the attachable tower cutting guide 400 demonstrating the lateral or outer surface 401 with the entry site of the obliquely oriented pin holes 318 for attachment of the guide to the bone. Multiple cutting tracks 320 aligned in a generally parallel array and disposed at a specified angle θ (preferably between 0 and 90 degrees) relative to the condylar rails when installed may be employed depending on the specific size of the desired bony cut and the desired anterior to posterior dimension of the femoral condylar graft to be transplanted. An anterior to posterior peg or hole or screw channel 322, is available for engaging attachable tower cutting guide to the cutting guide block 301 by placement of a metal peg through the peg hole and into the fixation hole 308 of the cutting guide block 301.

Figure 24:
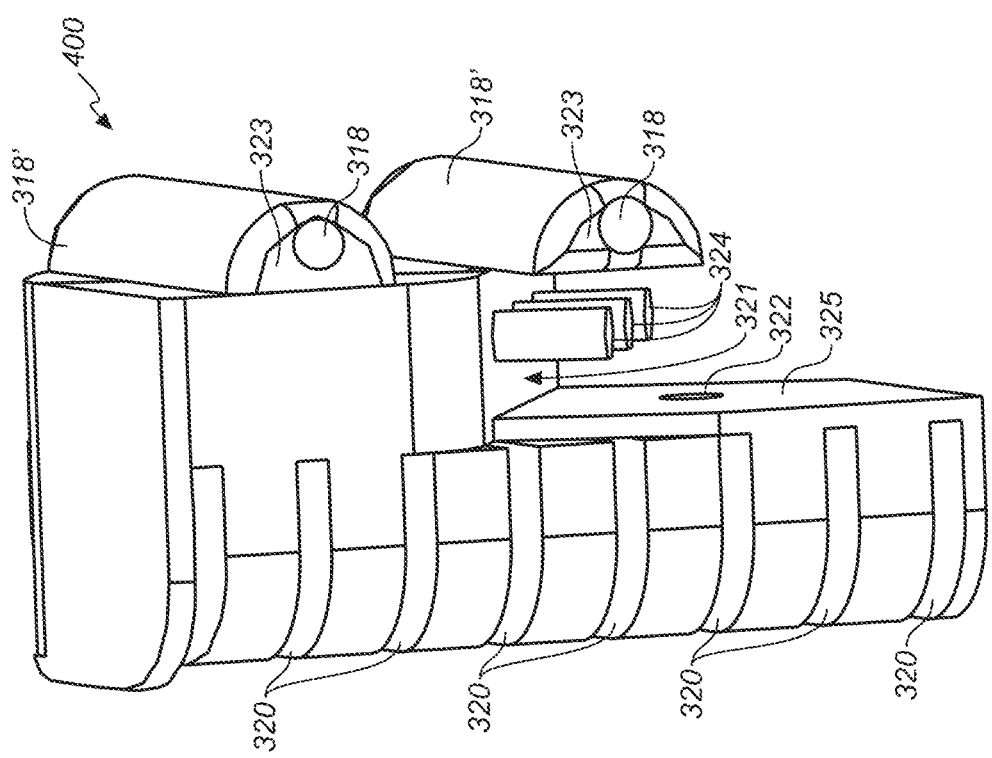
FIG. 24 is a lateral (medial) perspective view thereof.

FIG. 24 is a lateral perspective view of the attachable tower cutting guide 400 demonstrating the inner surface 323 with the exit site of the obliquely oriented pin holes 318 for attachment of the guide to the bone. Multiple cutting tracks 320 are again seen based on the specific size of the desired bone cut. The inner exit site of the anterior to posterior screw channel 322, is shown on the surface 325 that engages the distal portion 303 of the main cutting guide block 301 by placement of a metal screw through the screw hole and into the fixation hole 308 for the cutting guide block 301 of the main cutting guide 300.

Figure 25:
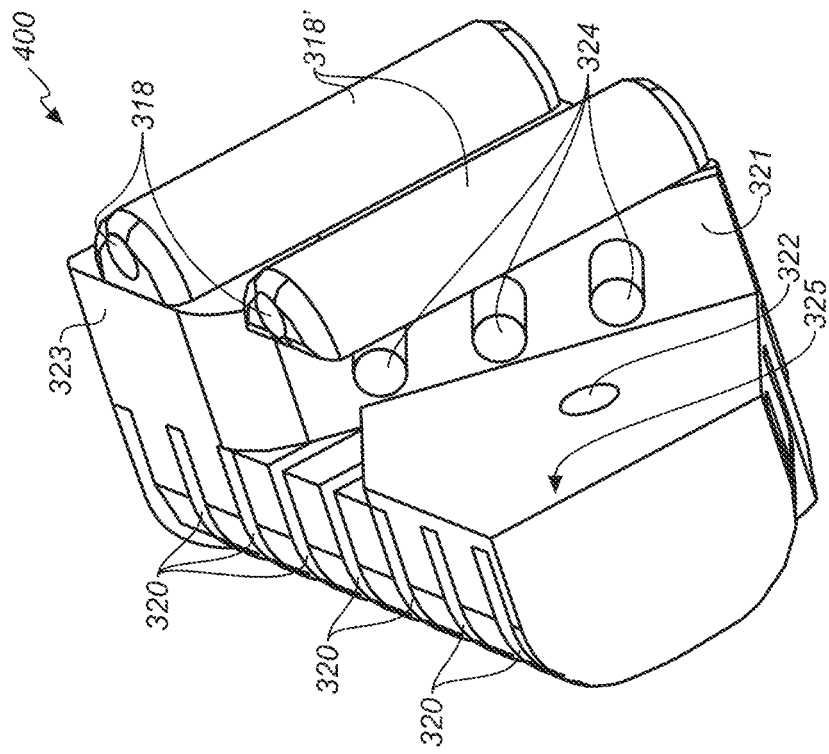
FIG. 25 is an inferior medial perspective view thereof.

FIG. 25 is an inferior perspective view of the attachable tower cutting guide 400 demonstrating the inner surface 323 with the exit site of the obliquely oriented pin holes 318 for attachment of the attachable tower cutting guide to the bone. Again, pin holes 318 are through holes and are disposed in sleeves or bosses 318N, which may be semi-cylindrical, though geometry is not critical. Multiple cutting tracks 320 are again seen, dimensions based on the dimensions of the femur being treated. The proximal exit site of the anterior to posterior screw hole 322 is again shown. Male pedestals 324 are shown to extend from the undersurface 321 of the attachable tower cutting guide for insertion into the superior cylindrical female elements 316 of the anterior surface 319 of the distal portion 303 of the main cutting guide block 301.

Figure 26:
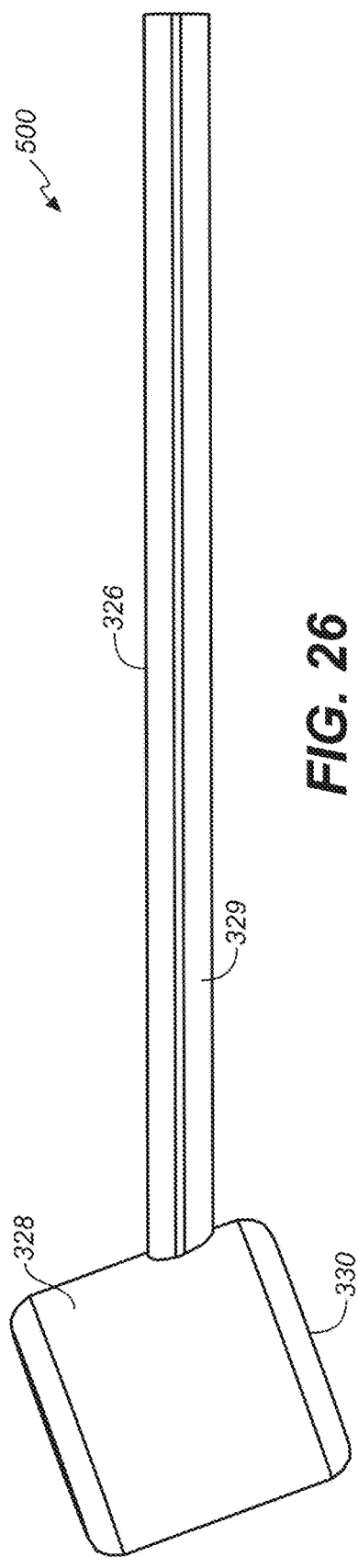
FIG. 26 is a lateral view in elevation of a screw guide, including a guide positioning arm, guide body, and screw aperture.

FIG. 26 is the lateral view of the screw guide 300 showing that it includes an elongate guide positioning arm 326, a generally cylindrical screw guide body 328, and screw aperture 330 disposed through the guide body. The guide positioning arm 326 fits into the screw guide tracks 314, seen in FIGS. 20-21. As can be seen, the cross-sectional shape of the guide positioning arm 326 is generally rectangular and it is sized slightly smaller than the conforming rectangular aperture of the screw guide tracks 314 so as to slide easily and smoothly into and through the aligned screw guide tracks while minimizing proximal and distal movement. Preferably the plane of the larger rectangular dimension 327 is oriented normal to the axis 331 of the screw aperture 330, while the plane of the shorter rectangular dimension 329 is oriented generally parallel to the same axis.

Figure 27:
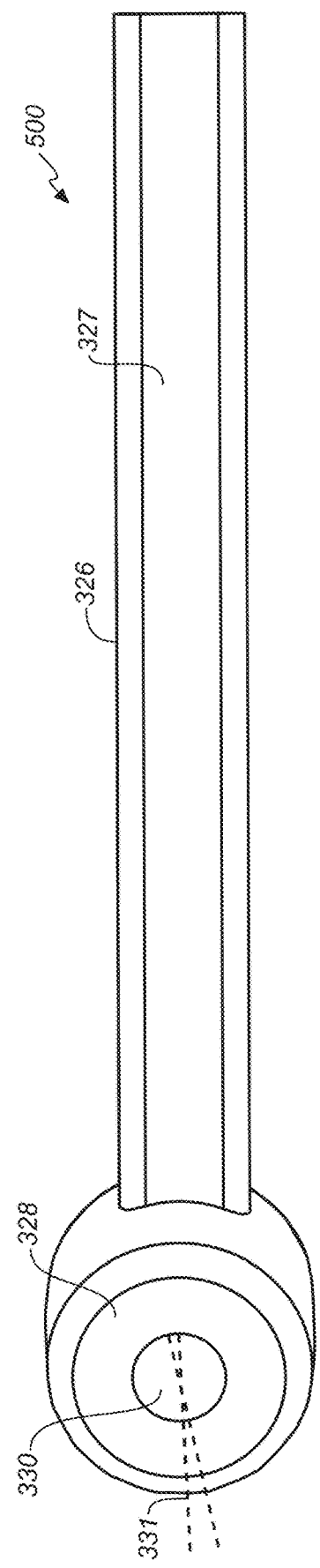
FIG. 27 is the anterior to posterior view in elevation thereof.
Figure 28:
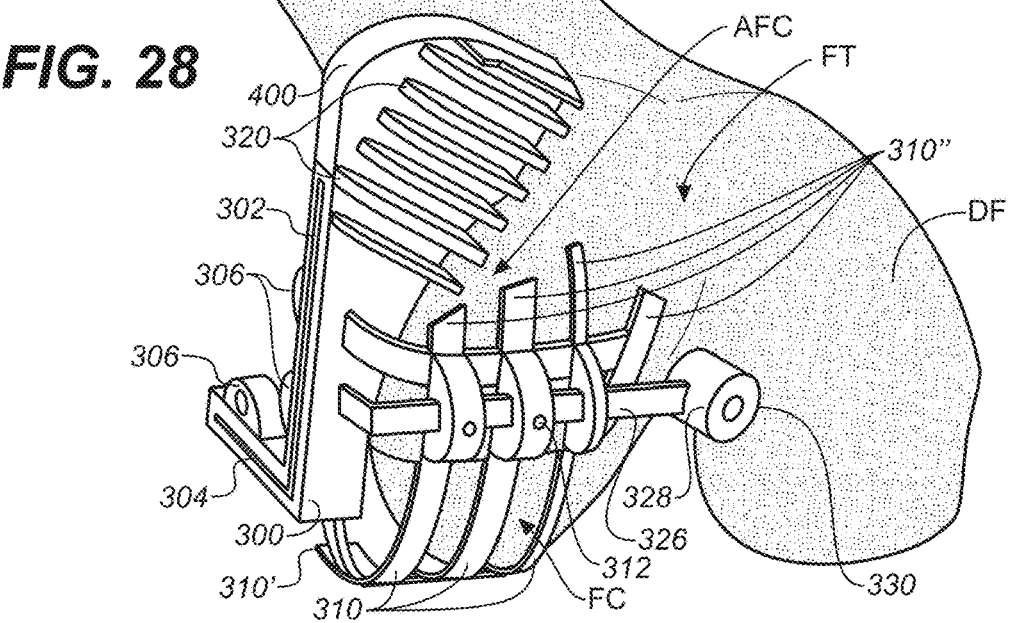
FIG. 28 is an inferior lateral perspective view of the assembled instrument complex consisting of the attachable tower interlocked with the femoral condylar cutting guide and applied to a right human distal femoral condyle (i.e. viewed anatomically from distal to proximal and slightly superiorly.

FIG. 27 is the anterior to posterior view of the screw guide, again showing the elongate guide positioning arm 326, the guide body 328, and the screw aperture 330. FIG. 28 is a perspective view of the entire instrument complex—cutting guide 300 and attachable tower cutting guide 400—as applied to a human distal femur DF. The main cutting guide 300 is shown with its distal cutting slot 302, and its posterior cutting slot 304. Fixation holes 306 in the main cutting guide demonstrate the contact with the femoral condyle FC for passage of the fixation pins (not shown). The condylar rails 310 rest on the anterior femoral condyle AFC up to the level of the femoral trochlea FT, and extend along the entire articular surface of the femoral condyle FC. Along the distal aspect, bolt hole 312 (bolt not shown) is provided for passage and insertion of a stabilizing bolt for stabilizing and securing the screw guide positioning arm 326 within the screw guide track 314. The screw guide body 328, and screw aperture 330 are shown and indicate the utility of the sliding positioning arm in allowing appropriate positioning of the screw away from the articular cartilage surface of the femoral condyle FC, as needed and such that fixation can be achieved in the non-articulating portion of the femoral condyle, based on the width of the condyle. The attachable tower guide 400 is shown and demonstrates the multiple cutting tracks 320, available for cutting of the condyle-trochlear interface of the diseased distal femur or the femoral allograft. The selected cutting track dictates the anterior-to-posterior length of the femoral graft and must be exactly matched between the recipient and the donor to ensure appropriate sizing of the graft.

Figure 29:
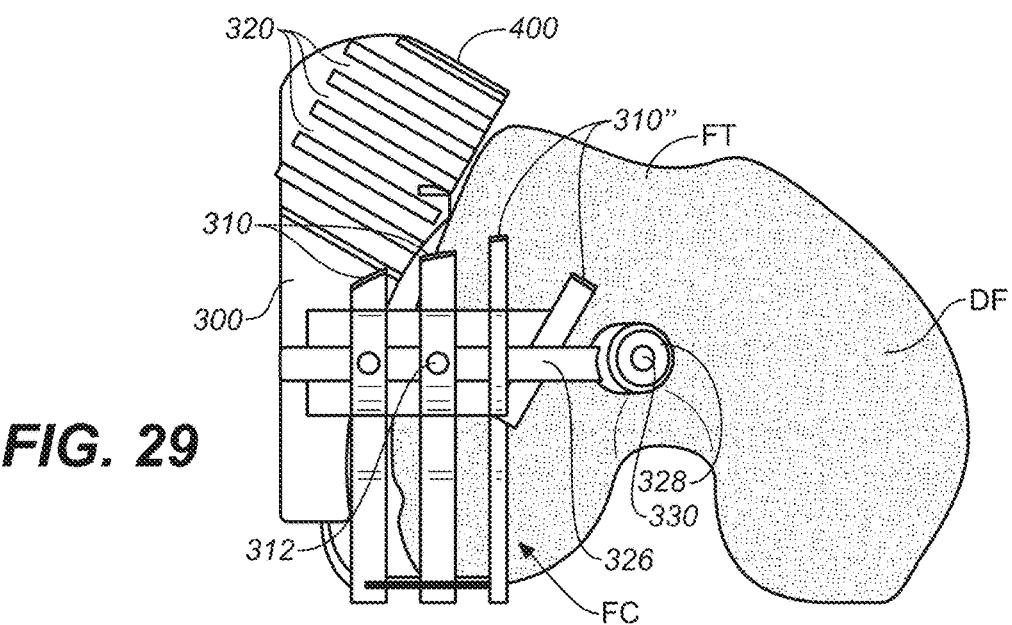
FIG. 29 is an inferior view in elevation thereof.

FIG. 29 is a distal view of the entire instrument complex as applied to a human distal femoral condyle FC. The femoral condylar cutting guide is shown with its condylar rails 310, resting on the entire femoral condyle FC to the level of the trochlea and extending posteriorly along the articular surface. At the distal most aspect of the guide there is a track 314, (not shown) for the screw guide positioning arm 326, with the bolt hole 312, (bolt not shown) for stabilization of the screw guide positioning arm 326. The screw guide body 328, and screw aperture 330 are shown. The tower cutting guide is shown and demonstrates the multiple cutting tracks, 320 available for cutting of the trochlear interface of the femoral allograft.

Figure 30:
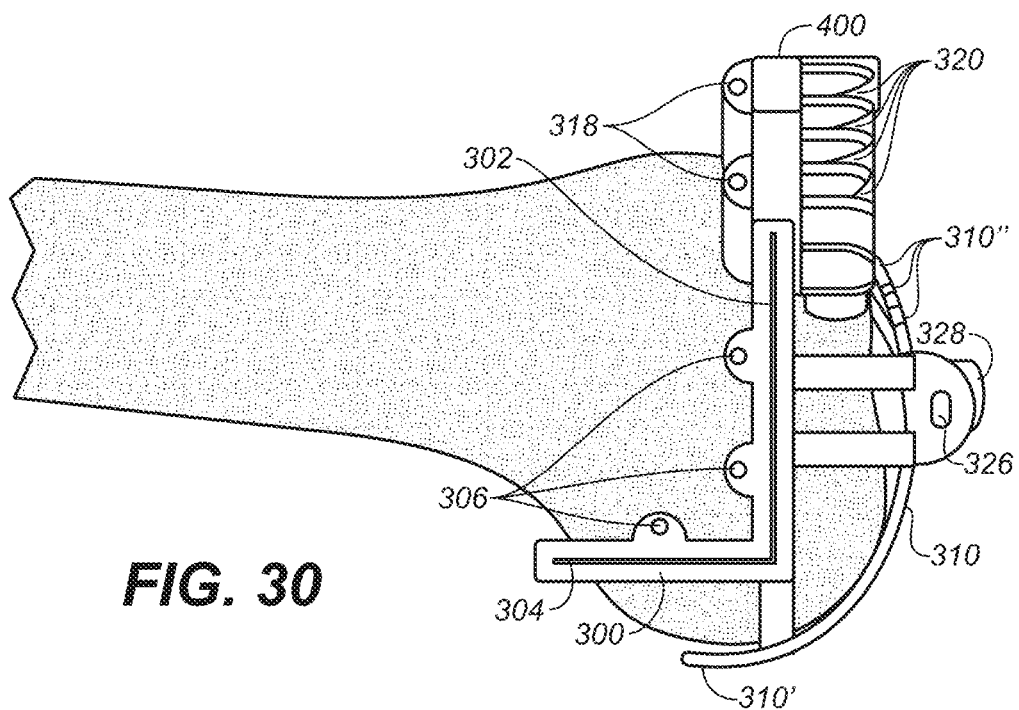
FIG. 30 is a right lateral view in elevation thereof.

FIG. 30 is a lateral view of the entire instrument complex as applied to a human distal femur. The main cutting guide is shown with its condylar rails 310, resting on the femoral condyle. At the distal most aspect of the guide the track for the screw guide positioning arm 326 is shown, along with the screw guide body 328. The attachable tower cutting guide 400 is shown and again demonstrates the multiple cutting tracks 320 available for cutting of the trochlear interface of the femoral allograft. Attached to the proximal aspect of the attachable tower cutting guide, there are obliquely oriented pin holes for attachment of the guide to the bone 318.

Figure 31:
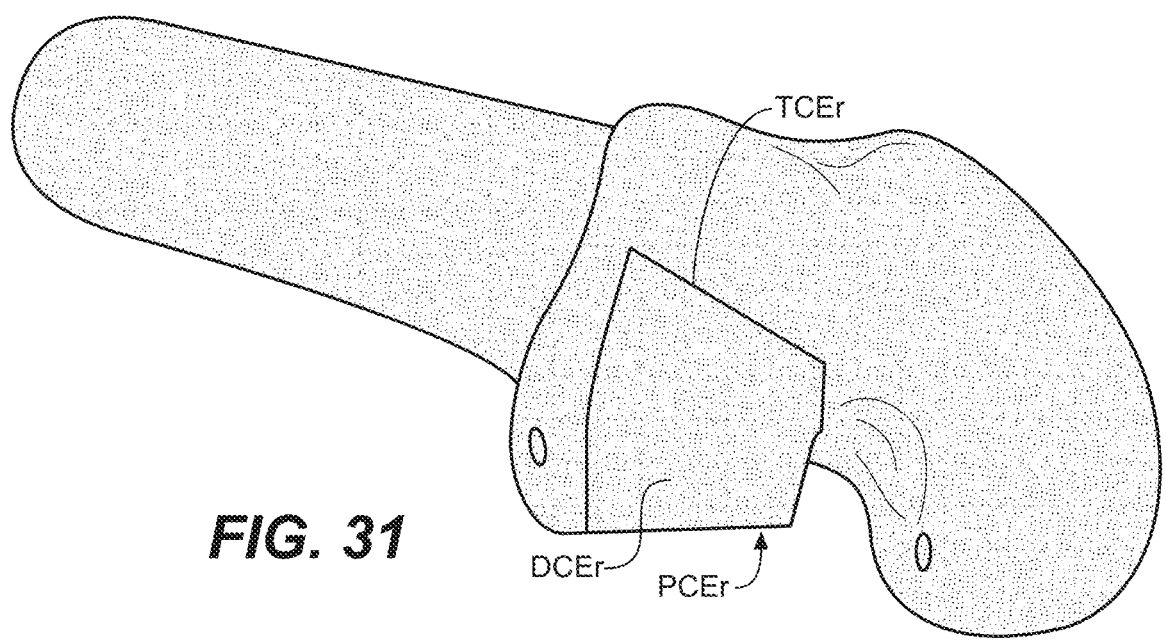
FIG. 31 is a perspective view of the patient's left femur after removal of the diseased medial femoral condyle so as to form the patient's femoral condyle recipient site.

FIG. 31 is a perspective view of a recipient patient's femur after removal of the diseased femoral condyle. Shown is the distal femoral cut edge DCEr, the trochlear cut edge TCEr, and the posterior femoral condyle cut edge PCEr.

Figure 32:
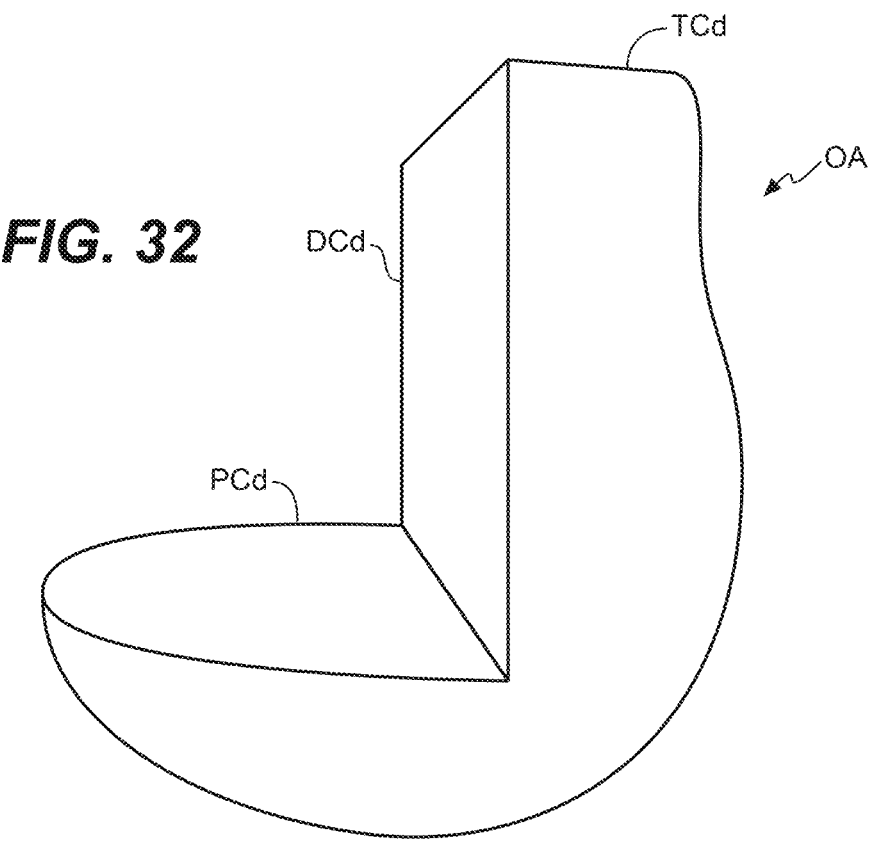
FIG. 32 is a lateral view of a femoral condyle osteochondral allograft after removal from the entire distal femoral allograft.

FIG. 32 is a lateral view of the donor's femoral condyle osteochondral allograft OA after it has been removed from the rest of the femoral condyle graft and indicating the position of the trochlear cut TCd, the distal femoral cut DCd, and the posterior condylar cut PCd.

Figure 33:
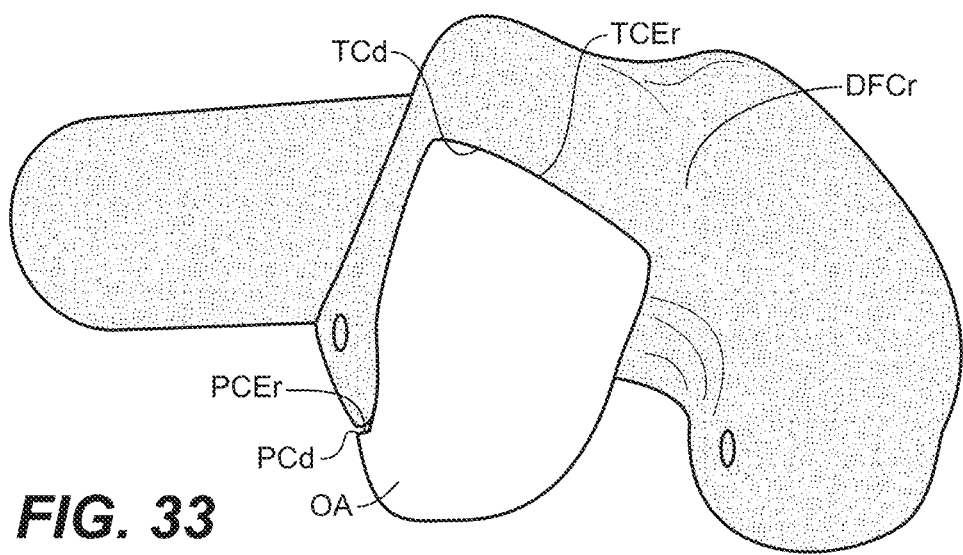
FIG. 33 is a perspective view of the osteochondral allograft after placement on the distal end of the patient's femoral condyle recipient site.

FIG. 33 is a perspective view of the osteochondral allograft after it has been placed on the distal end of the patient's distal femoral condyle recipient site. The patient's distal femur DFCr is shown. The cut trochlear edge TCEr is indicated as well as the posterior condylar edge PCEr.

Figure 34:
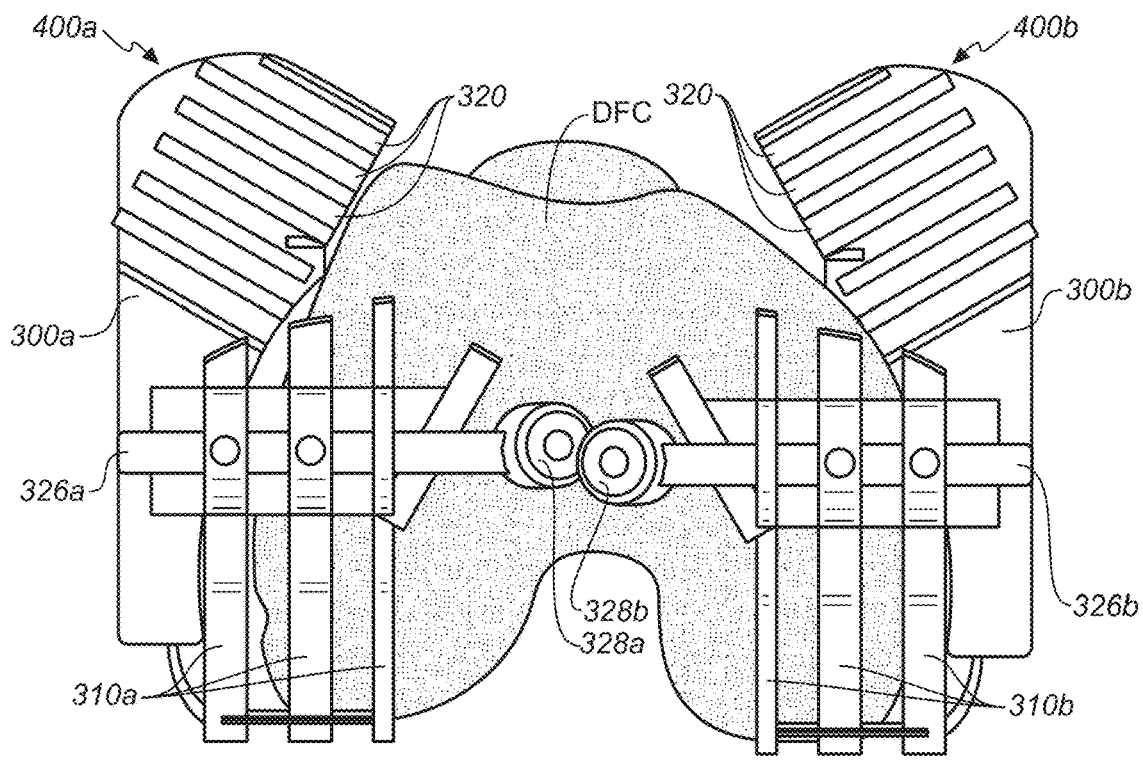
FIG. 34 is a right lateral view in elevation of symmetrical (mirror image) femoral condylar cutting guides applied to the end of a distal femur taken from the same perspective as that of FIG. 29.

FIG. 34 is a distal view of two mirror image (medial and lateral) guides applied to the end of the distal femur. They can each be stabilized to their independent femoral condyle with an independent locking screw guide 328a and 328b. The trochlea can be prepared using the attachable tower cutting guide(s) as shown 400a and 400b.

Figure 35:
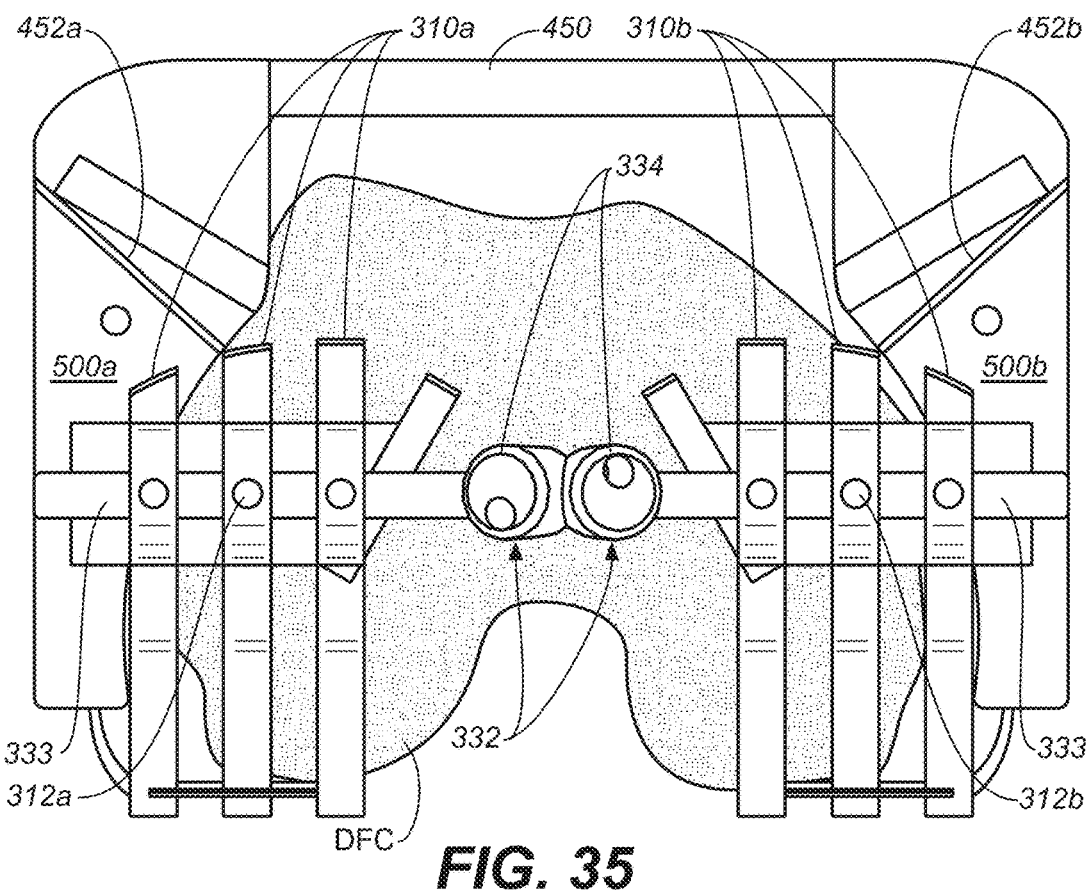
FIG. 35 is a front view in elevation of the symmetrical (mirror image) femoral condylar cutting guides applied to the end of the distal femur, and further including a mounted monoblock trochlear harvesting tower, a guide with placing the two trochlear cutting slots at a set distance and angle from one another and converging at a predetermined line.

FIG. 35 is a distal view of two mirror image cutting guides 300a, 300b, (no labels on this figure) applied to the end of the distal femur DFCr. An alternative embodiment is shown for a singular or monoblock trochlear guide 450 which rests on the medial and lateral guides. The condylar guides 300a, 300b are shown with their condylar rails 310a, 310b, and bolt holes 312a, 312b, which in this case are holding a single rigid connection rod 332 consisting of two attached screw guide bodies 334 in the midportion of an extended guide positioning arm 333. The rigid connection rod maintains the two mirror image guides in a collinear orientation facilitating the precision of the procedure.

The singular or monoblock trochlear guide consists of angled cutting surfaces 452a and 452b, which are disposed in angular deviations between 0 degrees and 180 degrees between the two sides. The plane of the two cutting surfaces meet at a line oriented parallel to the articular surface of the trochlea. The singular or monoblock trochlear guide facilitates en bloc removal of the diseased trochlea and harvesting of an identically sized osteochondral allograft trochlea.

Figure 16:
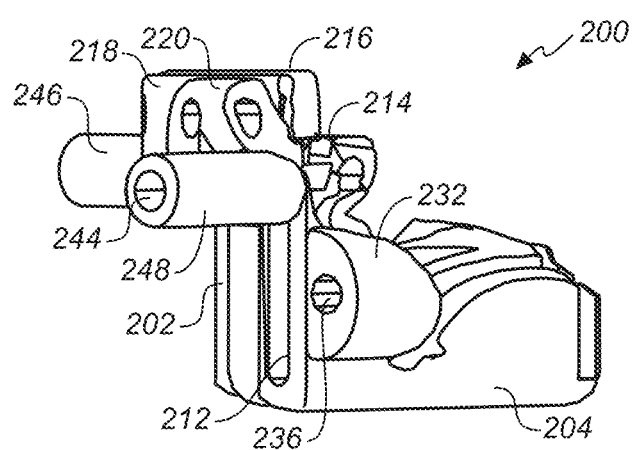
FIG. 16 is a lateral view of the monoblock acetabular cutting tool.
Figure 17:
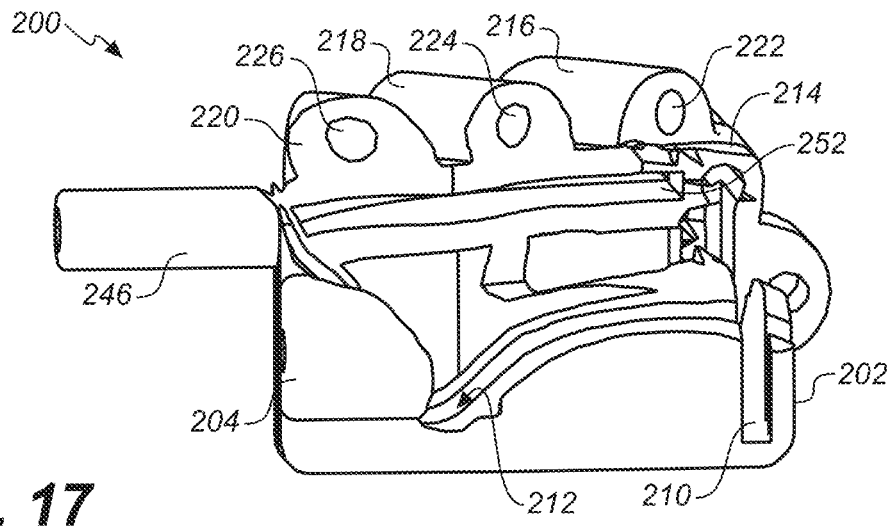
FIG. 17 is an inner perspective view of the monoblock acetabular cutting tool.
Figure 18:
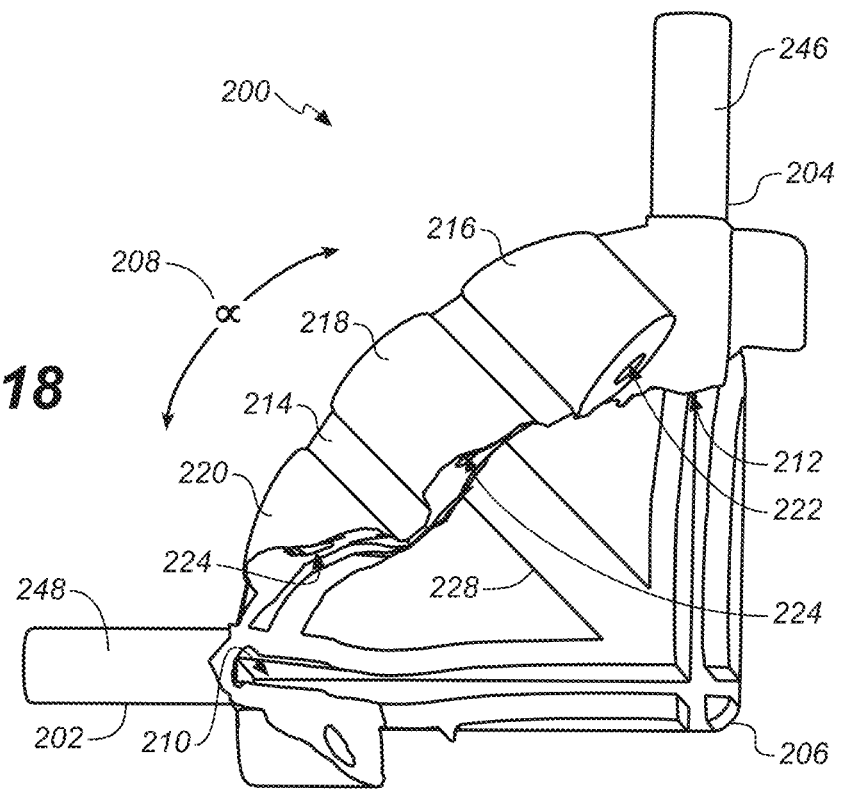
FIG. 18 is a superior view of the monoblock acetabular cutting tool.
Figure 19A:
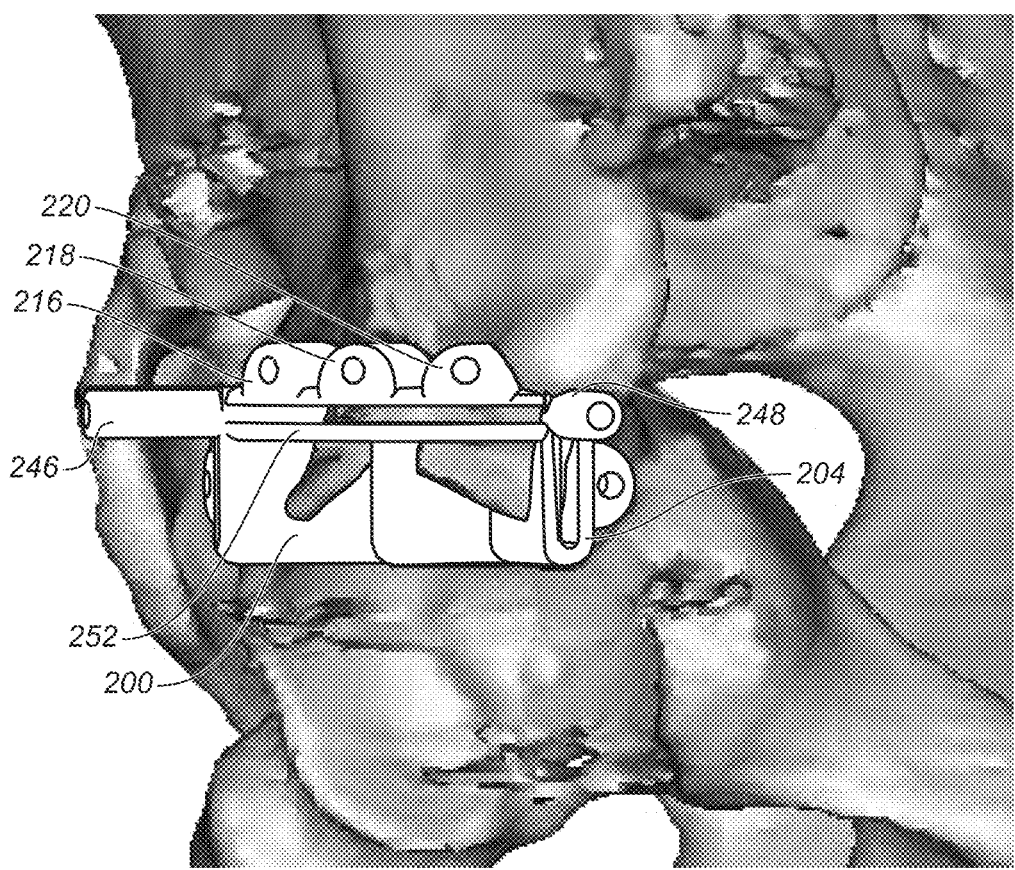
FIG. 19A is a lateral view of the human pelvis and the monoblock acetabular cutting tool installed thereon.
Figure 19B:
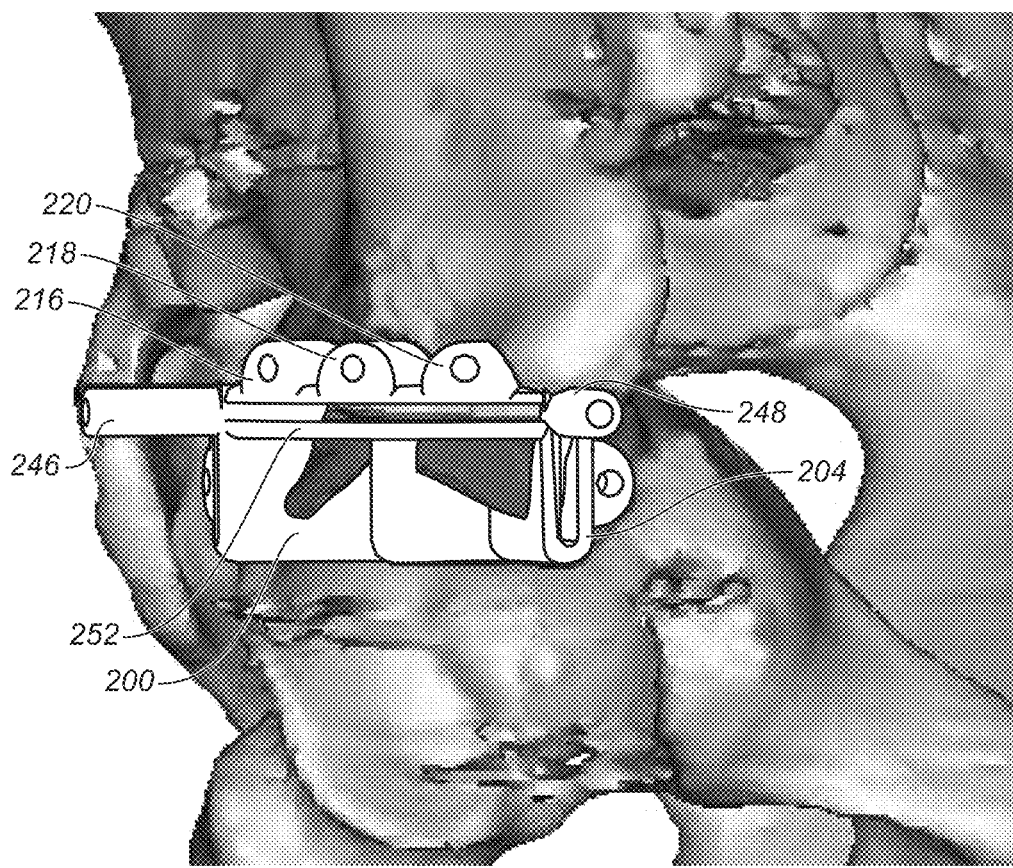
FIG. 19B is the same view showing the pelvis readied for removal of a bone segment.
Figure 19C:
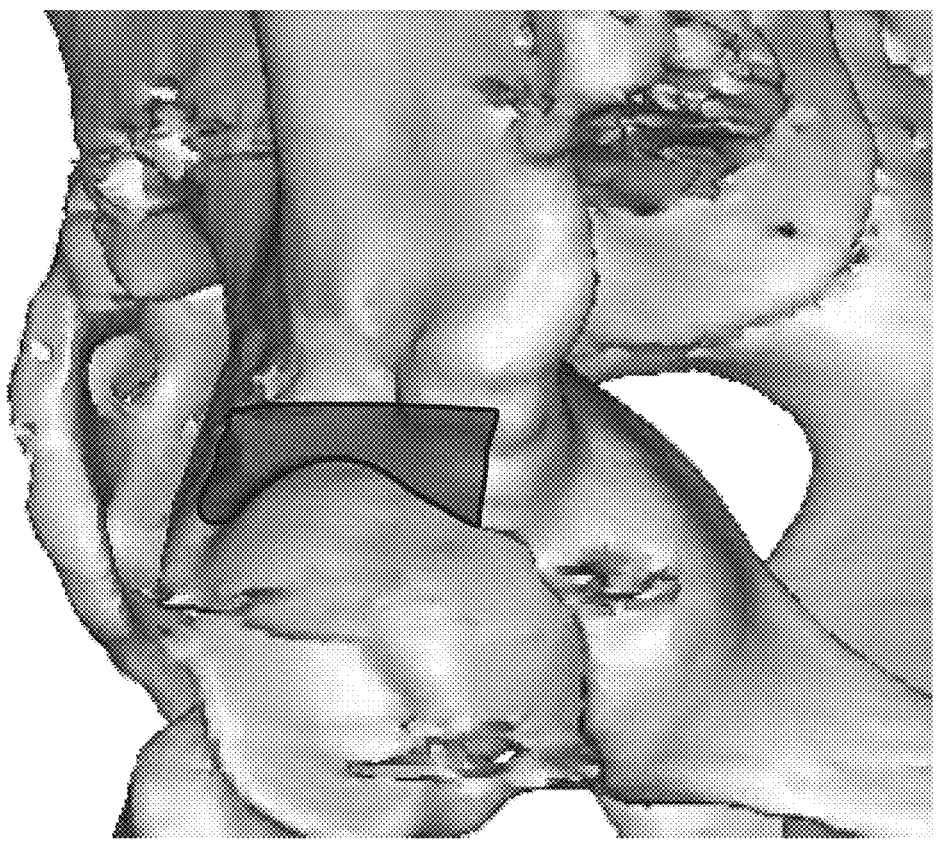
FIG. 19C is the same view showing the bone segment defined for removal.
Figure 19D:
FIG. 19D shows the pelvis with the segment removed.
Figure 19E:
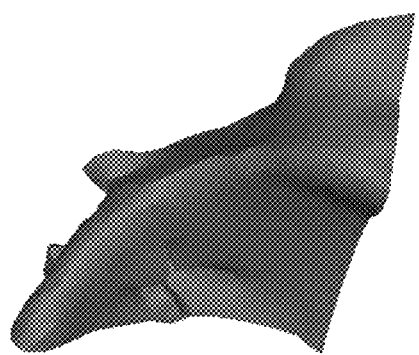
FIG. 19E is a view in the same orientation as that of FIG. 19D showing the bone segment removed.
Figure 36:
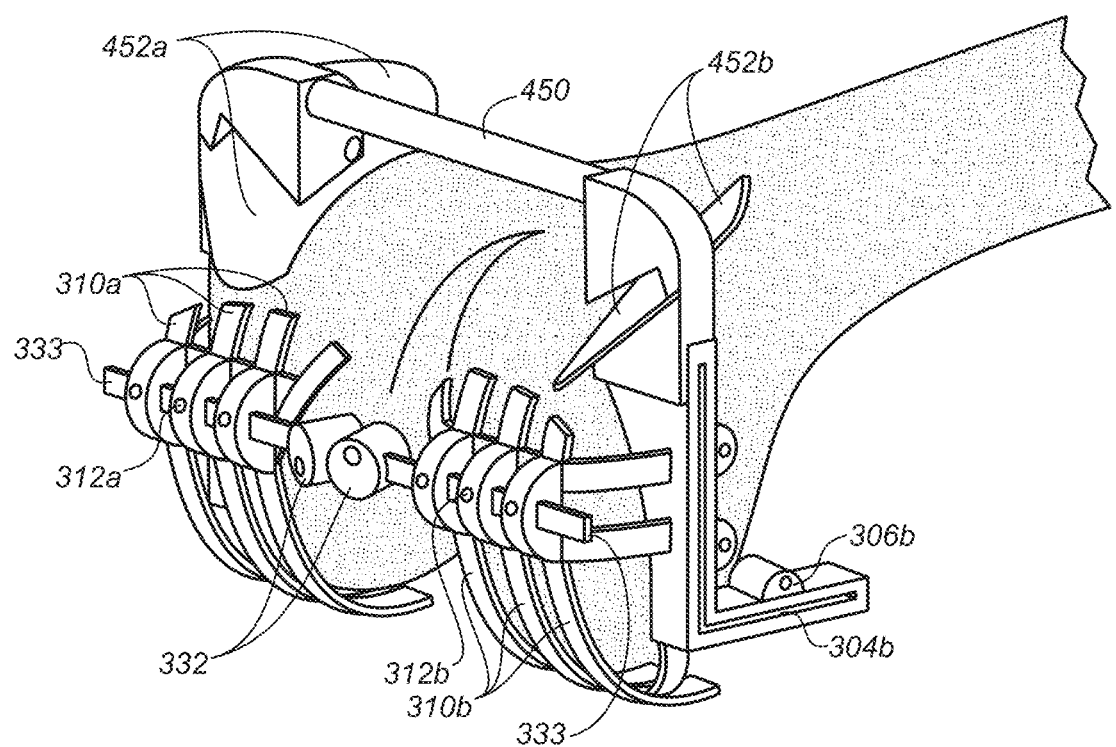
FIG. 36 is an upper front right perspective view of the symmetrical (mirror image) guides applied to the end of the distal femur with the mounted monoblock trochlear harvesting tower also installed.
Figure 37:
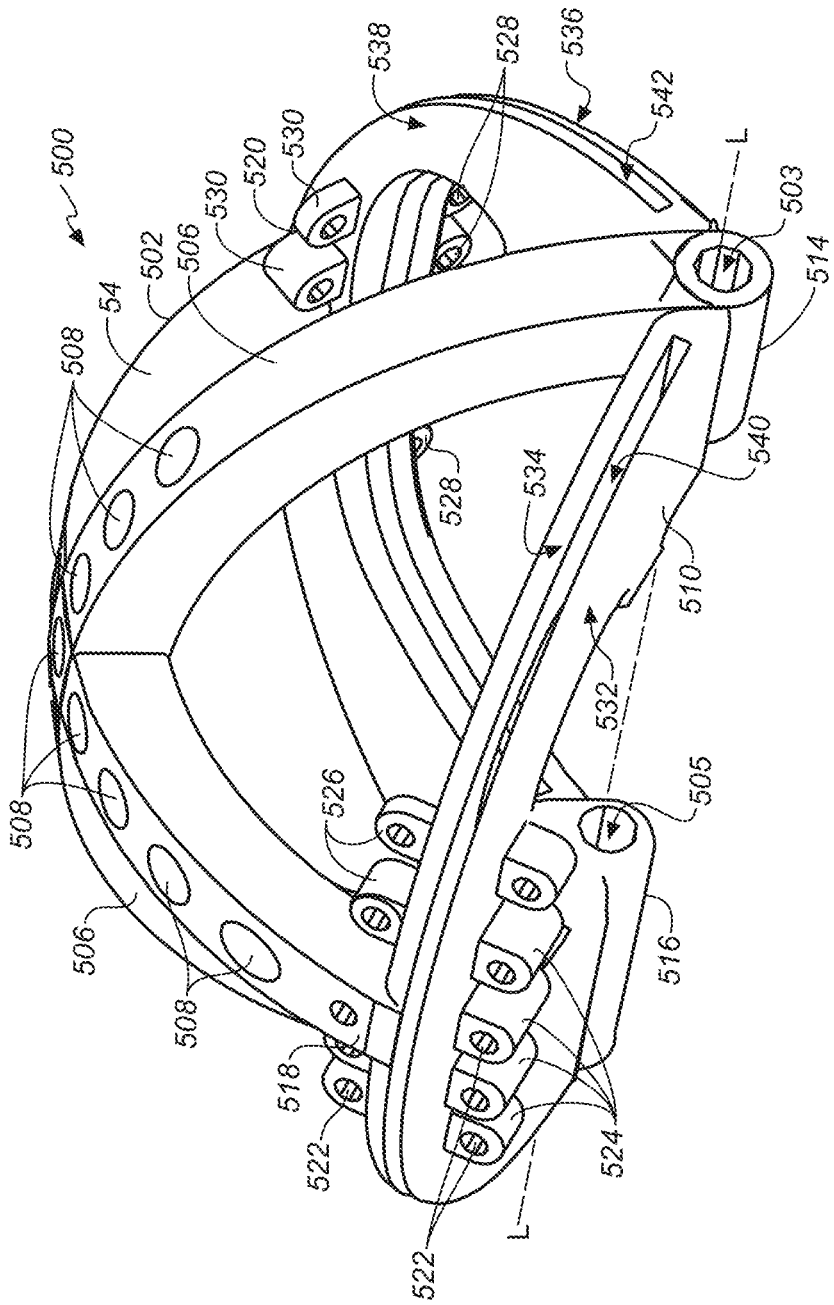
FIG. 37 is a perspective view of an embodiment of the bone cutting guide system of the present invention—the trochlear cutting guide.
Figure 38:
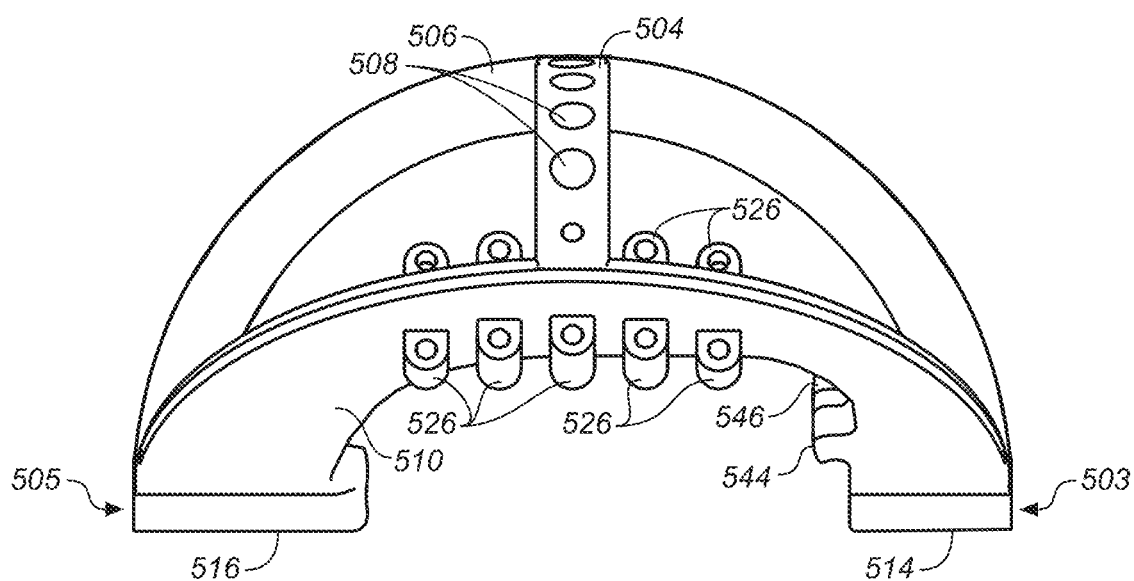
FIG. 38 is a lateral view of the trochlear cutting guide.
Figure 39:
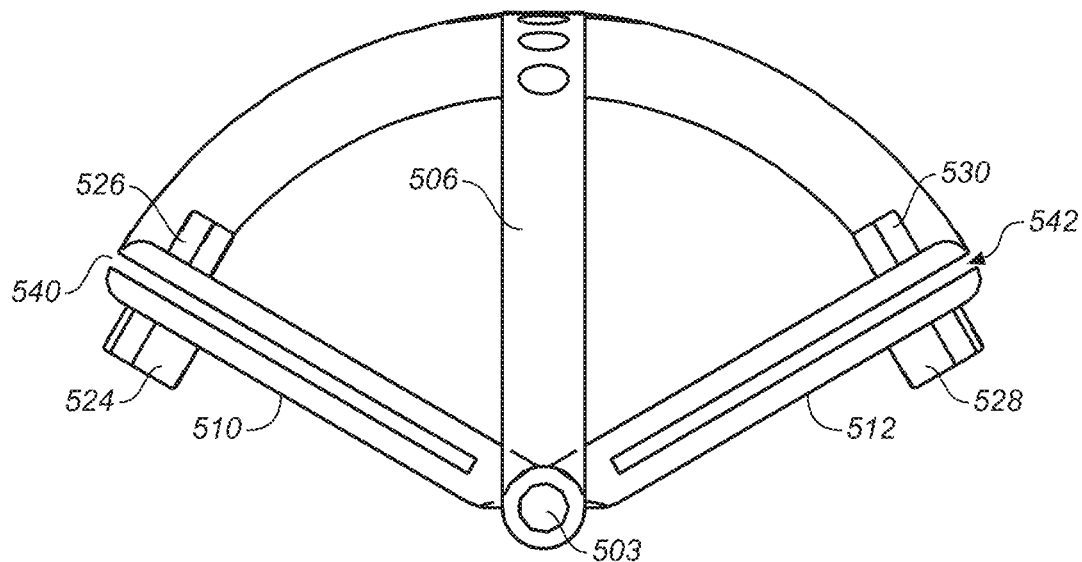
FIG. 39 is a distal view of the trochlear cutting guide showing its distal cylindrical channel.
Figure 40:
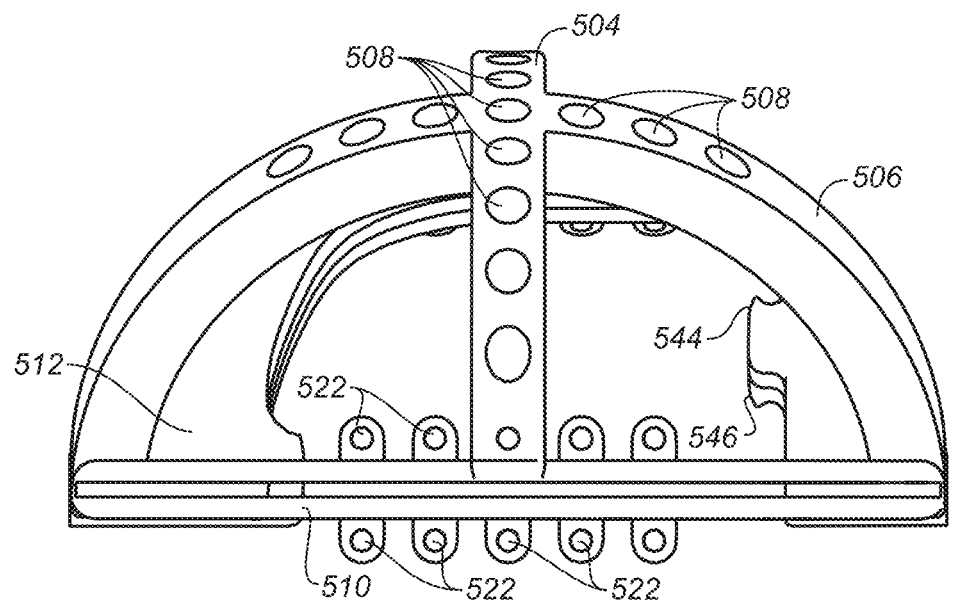
FIG. 40 is a lateral view of the trochlear cutting guide.
Figure 41:
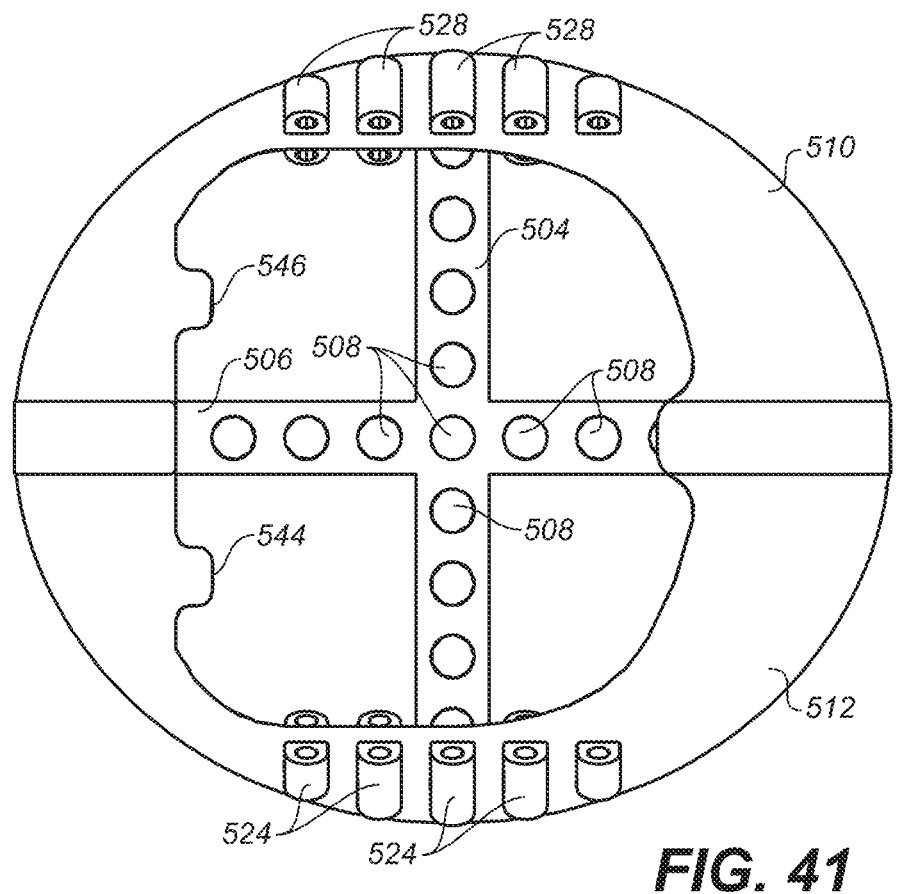
FIG. 41 is an inferior view of the trochlear cutting guide.

FIG. 36 is a distal perspective view of the apparatus from FIG. 16 showing the condylar guides with their condylar rails 310a, 310b, respectively, and corresponding bolt holes 312a, 312b, for holding the rigid connection rod 332 with its extended guide positioning arms 333 and the singular or monoblock trochlear guide 450 with its angled cutting surfaces 452a, 452b. The posterior cutting slot 304b and fixation hole 306b of the condylar guide are also shown. The combination of the posterior cutting slot 304b, distal cutting slot 306b, and trochlear cutting surfaces 452a, 452b facilitates the recovery of the entire distal articular surface of the femur.

FIGS. 37-54 show another embodiment of the present invention, these views featuring a dedicated trochlear cutting tool 500 that allows a surgeon to recover the entire trochlea as one large segment while leaving the medial and lateral femoral condyles untouched in order to transplant a normal healthy trochlear allograft or tissue-engineered trochlear implant to the matching geometry of a normal trochlea.

The embodiment of FIGS. 37-54 includes a stabilizing frame 502 having two intersecting arcuate beams, a short beam 504, and a long beam 506, each with multiple cylindrical holes 508 for insertion and placement of reference spacers 515. The reference spacers allow the cutting guide to be precisely positioned at a set distance above the complex surface of either the donor or recipient trochlea. Two arcuate cutting elements 510, 512, each describing approximately 180 degrees of arc are placed at the inferior aspect of the long beam 506 and converge in a virtual line L defined by holes 503, 505 through spaced apart distal and proximal coaxial tubes 514, 516, respectively. The ends 518, 520 of the short beam 506 connect to the middle of the arcuate cutting elements 510, 512, respectively. The cutting elements also include fixation holes 522 disposed through projecting bosses 524, 526, 528, 530 on the lower and upper surfaces 532, 534, 536, 538 of each cutting element, aligned (i.e., parallel to) the plane of the interior sides of the cutting slots of their respective cutting element.

Fixation pins or screws (not shown) inserted through the fixation holes are employed to hold the trochlear cutting guide against bone both above and below the cutting slots 540, 542 in the respective cutting elements, the cutting slots configured for passage of a bone cutting instrument such as a saw or burr. The cutting elements are placed at an angle of between 45 to 180 degrees to one another in the smallest angle between them allowing for removal of a bone segment as small as a small bone wedge or as large as the entire trochlea with a flat undersurface. In most applications an angle of approximately 120 degrees is ideal between the two bone cutting slots in the cutting elements.

The aligned coaxial distal and proximal holes 503, 503 of the tubes 514, 516 define a discontinuous cylindrical hole for placement of a fixation rod in the guide's distal and proximal aspects. Both the distal cylindrical hole 503 and the proximal cylindrical hole 505 are coplanar with the planes of the converging cutting slots and allow for fixation of the guide through bone by a rod passed through the distal cylindrical hole 503, then through the femoral bone, and then through the proximal cylindrical channel 505 (rod not shown).

Referring specifically to FIGS. 38, 40-41, 43 and 53, there is shown referencing platforms 544, 546 on a distal inner circumference of each of the arcuate cutting elements 510, 512 that makes contact with the articular cartilage surface ACS of the trochlea T and femoral condyle FC in order to ensure that the graft and the recipient site have an ideal surface match of their cartilage surface that the interface between graft and recipient site femoral condyles. The platform can be cylindrical, rectangular or any polygonal shape. It can be fixed to the guide or removable. In the embodiment illustrated herein, it is integral with the two cutting elements of the guide.

Figure 42:
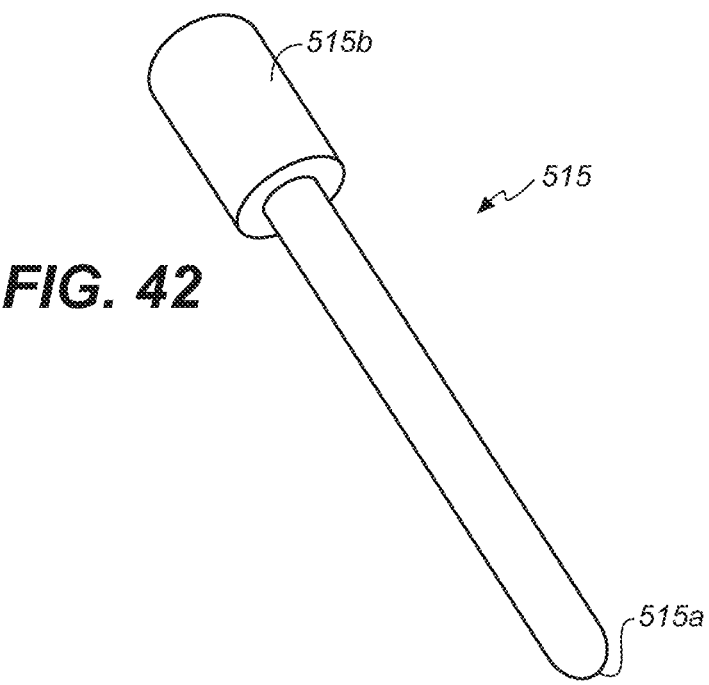
FIG. 42 is a perspective view of a reference spacer.
Figure 43:
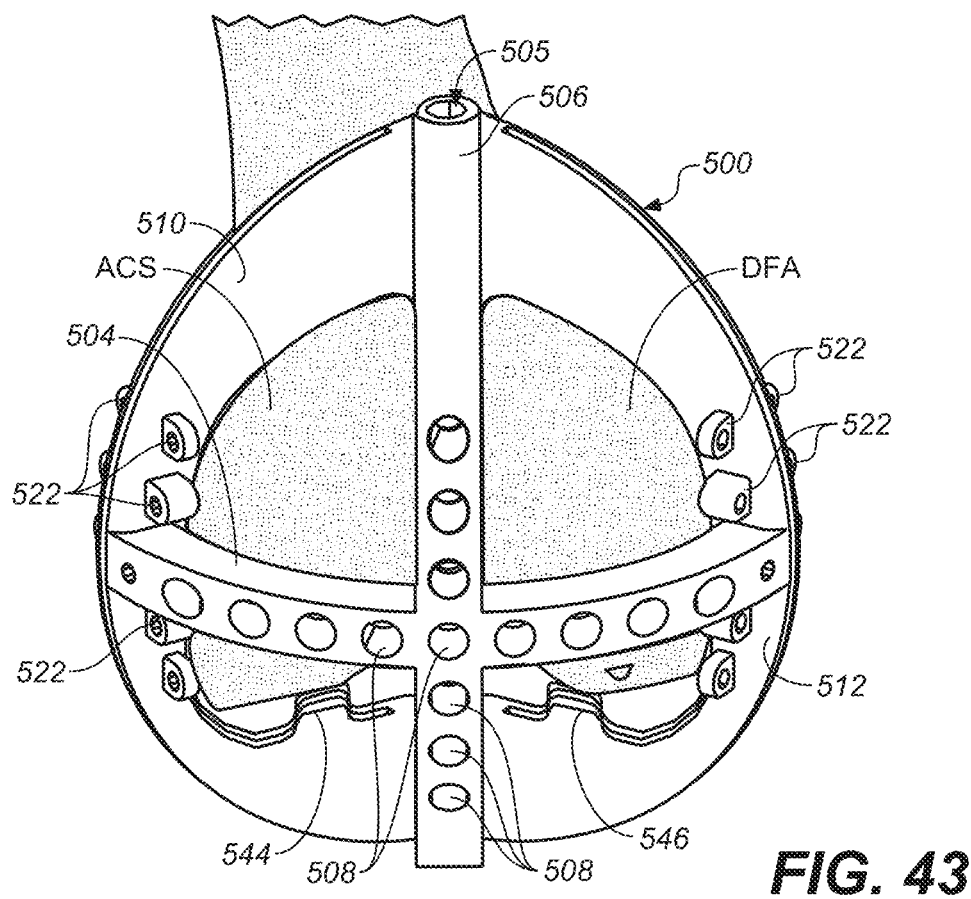
FIG. 43 is a superior view of the trochlear cutting guide placed on a distal femoral allograft.

FIG. 42 is a perspective view of a reference spacer 515, preferably configured generally cylindrically for easy passage through fixation holes 508. Distally, the spacer is disposed with a rounded edge 515a to avoid injury to the articular cartilage. The spacer has a proximal expansion 515b which allows for handing and insertion of the spacer. The spacer has an interference fit with the cylindrical holes 508 of the trochlear guide such that it can slide in and out but remains relatively stable during normal handling of the guide allowing a mapping of the surface of the trochlea between the donor and recipient. In embodiments, it can have radial cutouts to enable it to insert in discrete increments.

Figure 44:
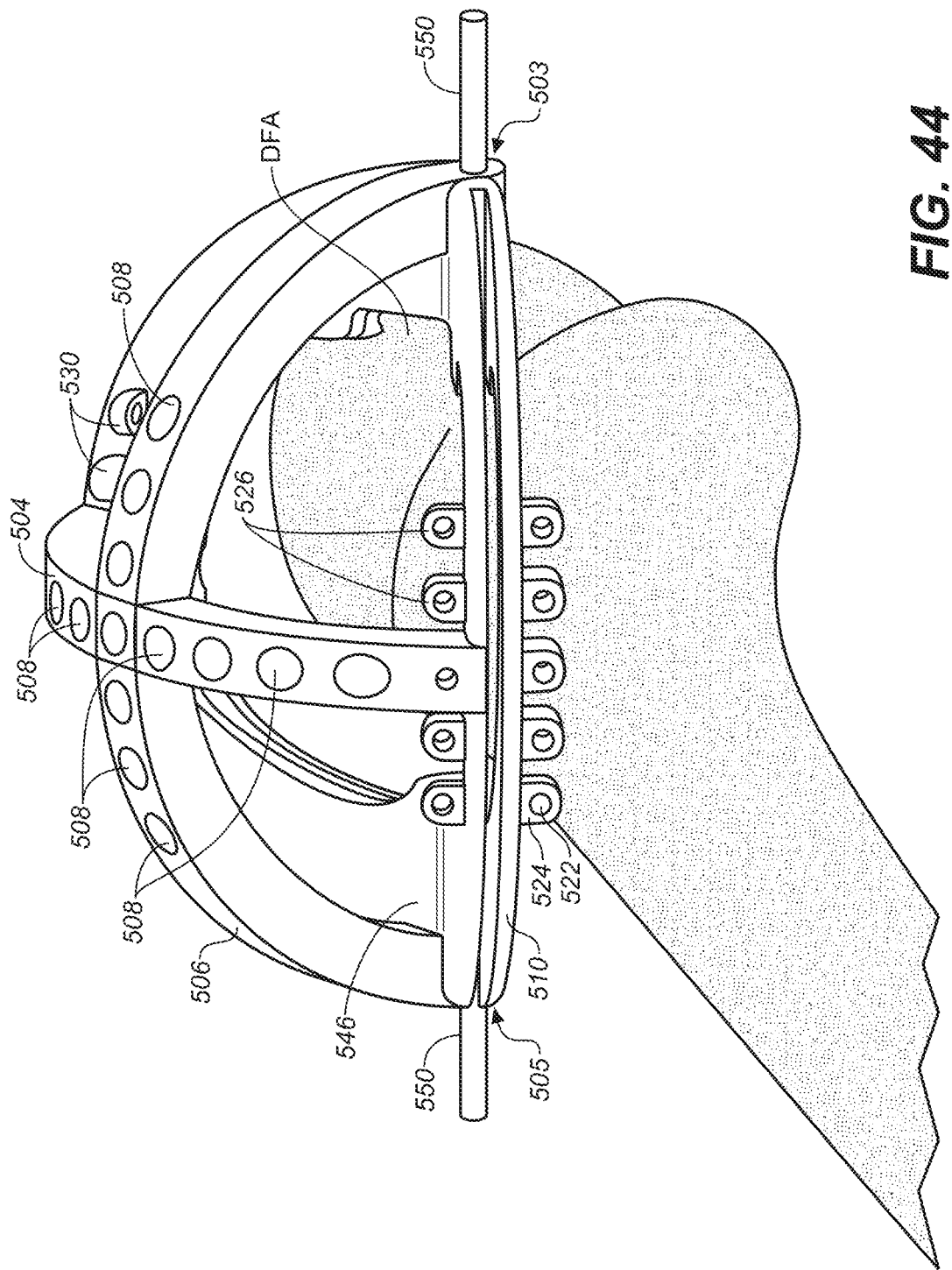
FIG. 44 is a lateral view thereof.

Looking now at FIGS. 43-46, there is shown a superior, lateral view, distal perspective, and distal view, respectively, of the trochlear cutting guide 500 with placement on a distal femoral allograft DFA. The referencing platforms 544, 546 on the distal inner circumference are shown. These makes contact with the articular cartilage surface of the trochlea to ensure that the graft and the recipient site have an ideal surface match with no excessive prominence of the graft at its interface with the normal femoral cartilage. FIG. 44 shows the holding rod 550 positioned directly on the line where the cutting planes of the cutting elements intersect and through coaxial holes 503, 505.

Figure 45:
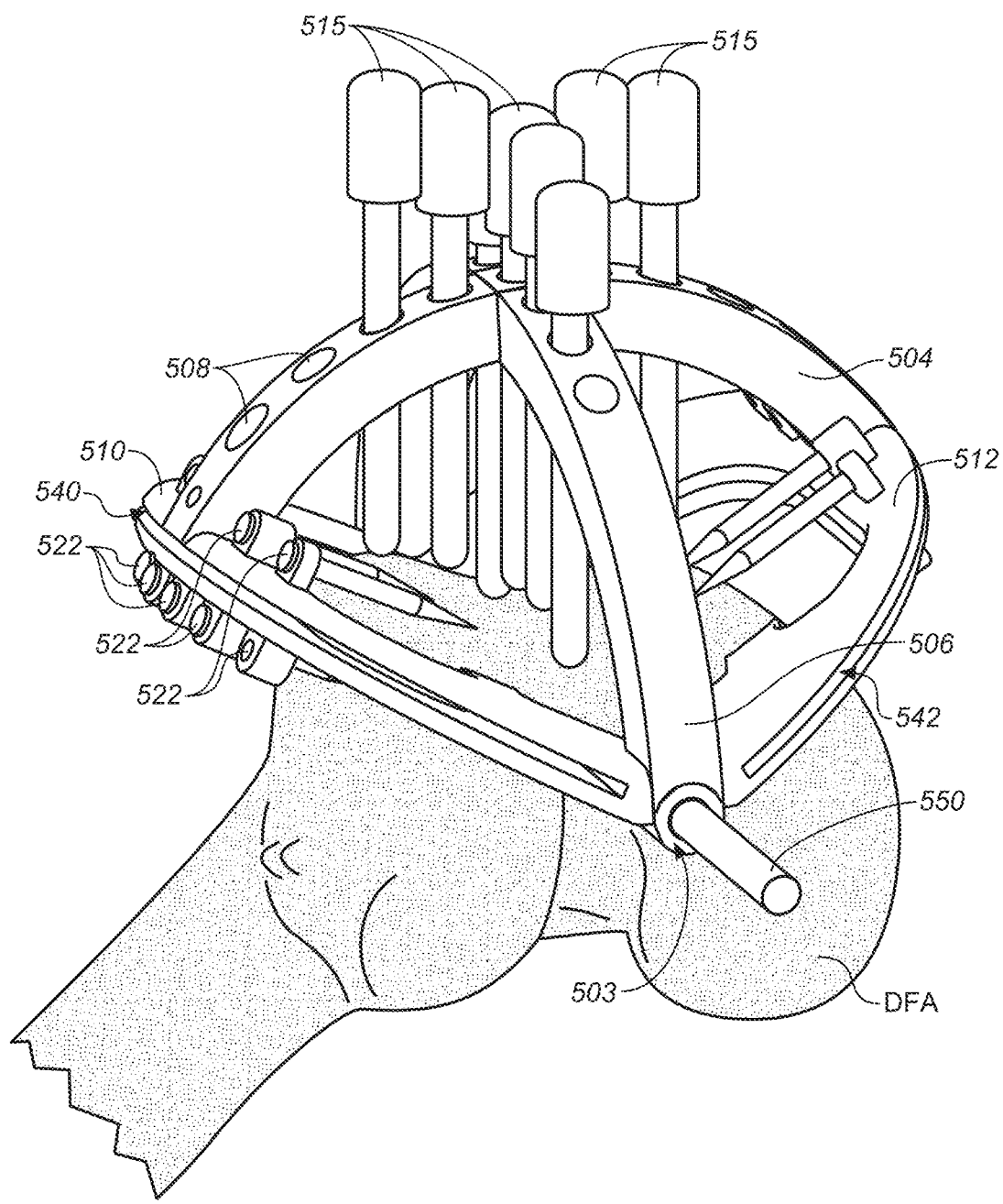
FIG. 45 is a distal perspective view thereof.
Figure 46:
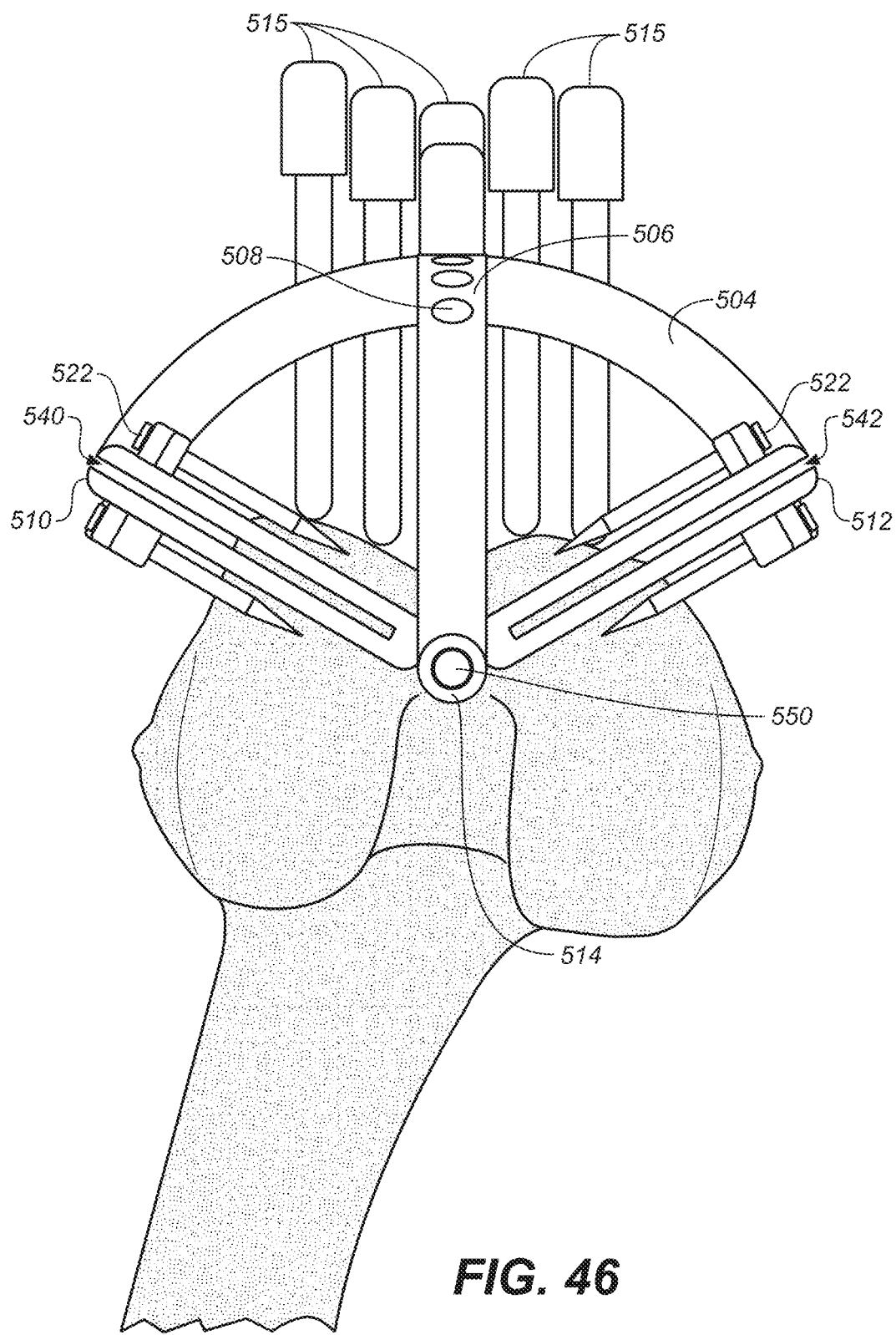
FIG. 46 is another distal view thereof, showing the trochlear cutting guide placed on a distal femoral allograft and featuring reference spacers disposed through multiple cylindrical channels to reference the bone surface of the graft.

FIGS. 45-46 illustrate placement of multiple reference spacers 515 within the guide to reference the surface of the graft. By placement of these spacers the trochlea guide is rotated in the axial plane such that it takes a symmetric thickness of bone from the medial and lateral trochlea from the donor allograft. The spacers also allow the guide to be positioned in line with the sulcus of the trochlea in the coronal plane. If needed, the holding rod 550 can be removed and reinserted after the placement of the referencing spacers.

Figure 47:
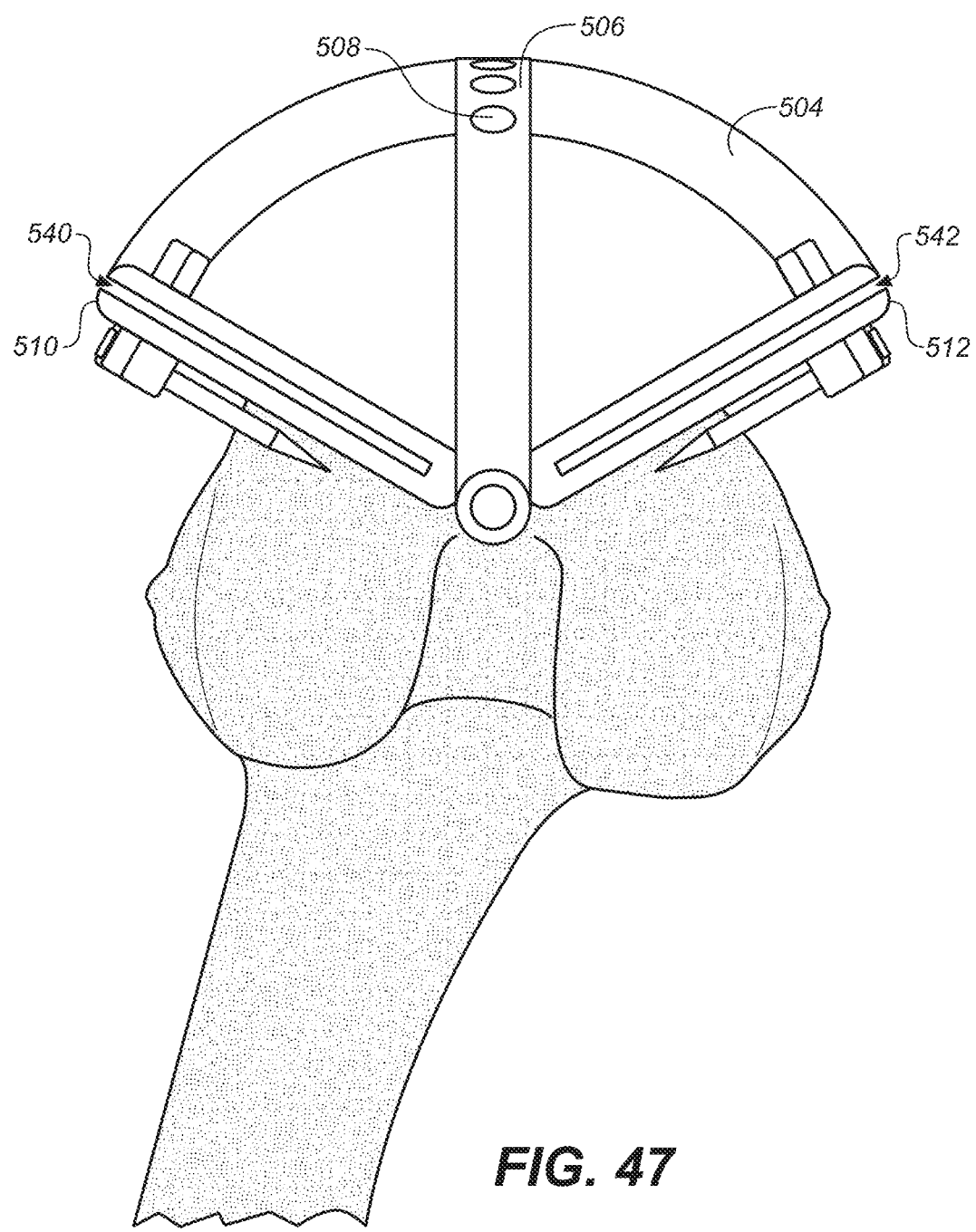
FIG. 47 is the same view showing the distal femoral allograft with a trochlear graft having been cut through the cutting channels and removed.

FIG. 47 is a distal view of the trochlear cutting guide placed on the distal femoral allograft wherein the graft G (shown in isolation in FIG. 48) has been cut through the cutting channels 540, 542 of the cutting elements 510, 512. The referencing spacers have been removed. The trochlear graft has been removed. The residual portion of the allograft is shown. In an alternate technique the referencing spacers can be left in place at the set depth for each spacer defining a desired three dimensional configuration of the spacer tips. The guide can be removed with the spacers remaining in place and can then be applied onto the surface of the diseased trochlea to achieve a perfect surface match between the donor and the recipient trochleae. This is a preferred technique if the diseased trochlea has a normal morphology.

Figure 48:
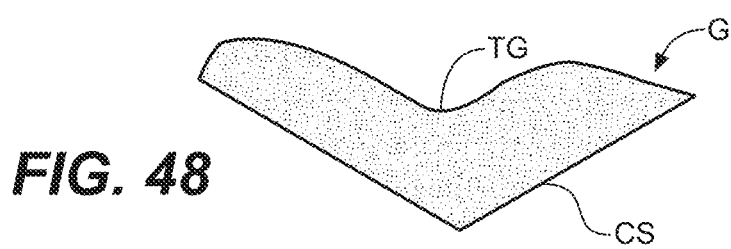
FIG. 48 showing the removed trochlea allograft specimen shown in isolation with a non-articular chevron-shaped triangular morphology.

FIG. 48 shows the trochlea allograft specimen G shown in isolation. The trochlear groove TG is shown as well as the cut segments CS cut through the cutting channels (542 AND 540) (not shown) intersecting at the virtual line of the holding rod 550 (not shown).

Figure 49:
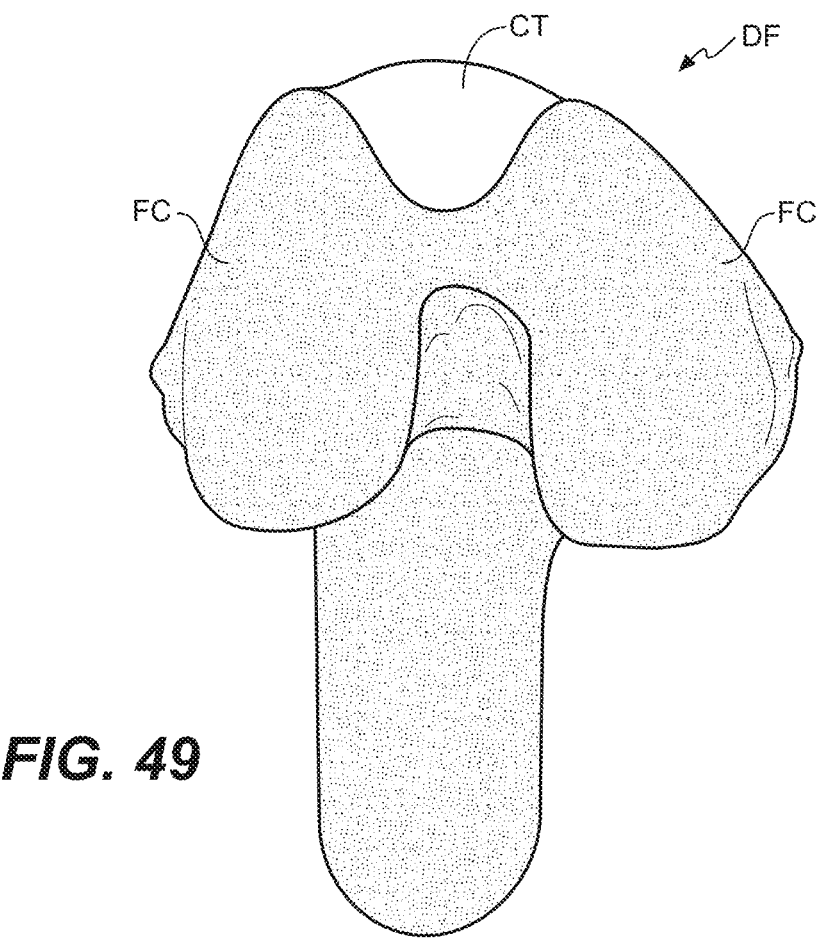
FIG. 49 is a distal view of a diseased femur with trochlear dysplasia.
Figure 50:
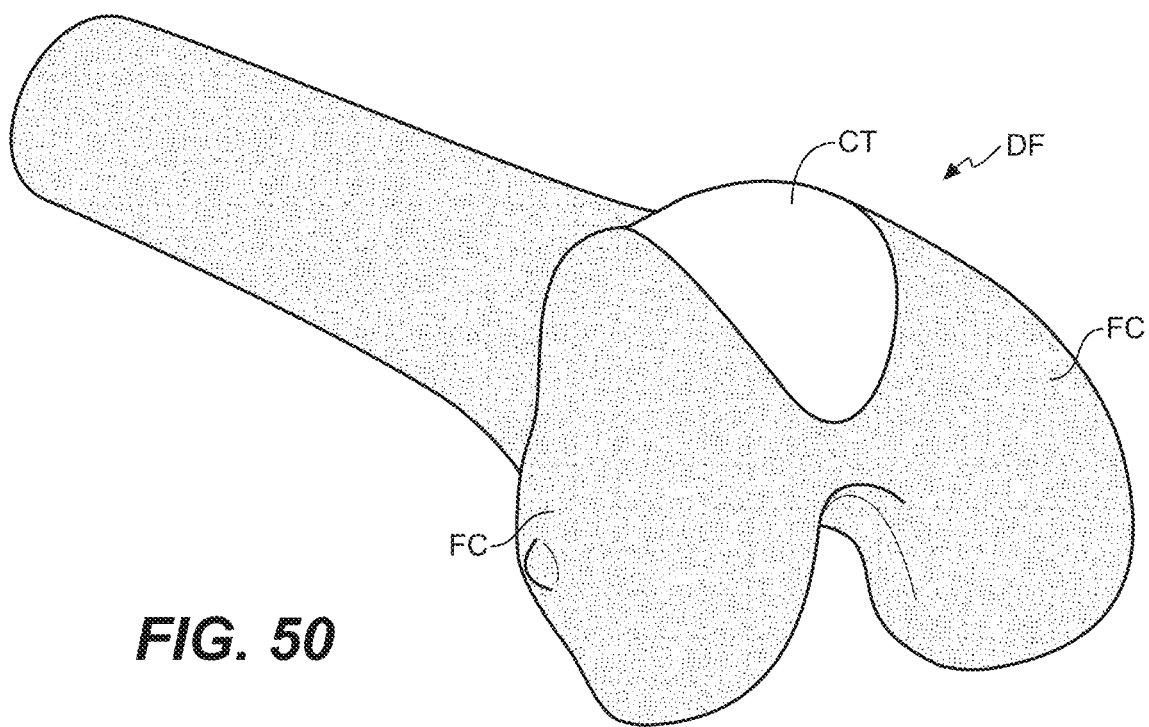
FIG. 50 is a distal perspective view of the same diseased femur with trochlear dysplasia.

FIGS. 49-50 are distal and distal perspective views, respectively, of a diseased femur DF which in this case has trochlear dysplasia, a disease process where there is no concavity for tracking of the patella and where the trochlea is instead convex in morphology—in this instance the trochlea with a convex morphology CT is shown. The femoral condyles FC are normal.

Figure 51:
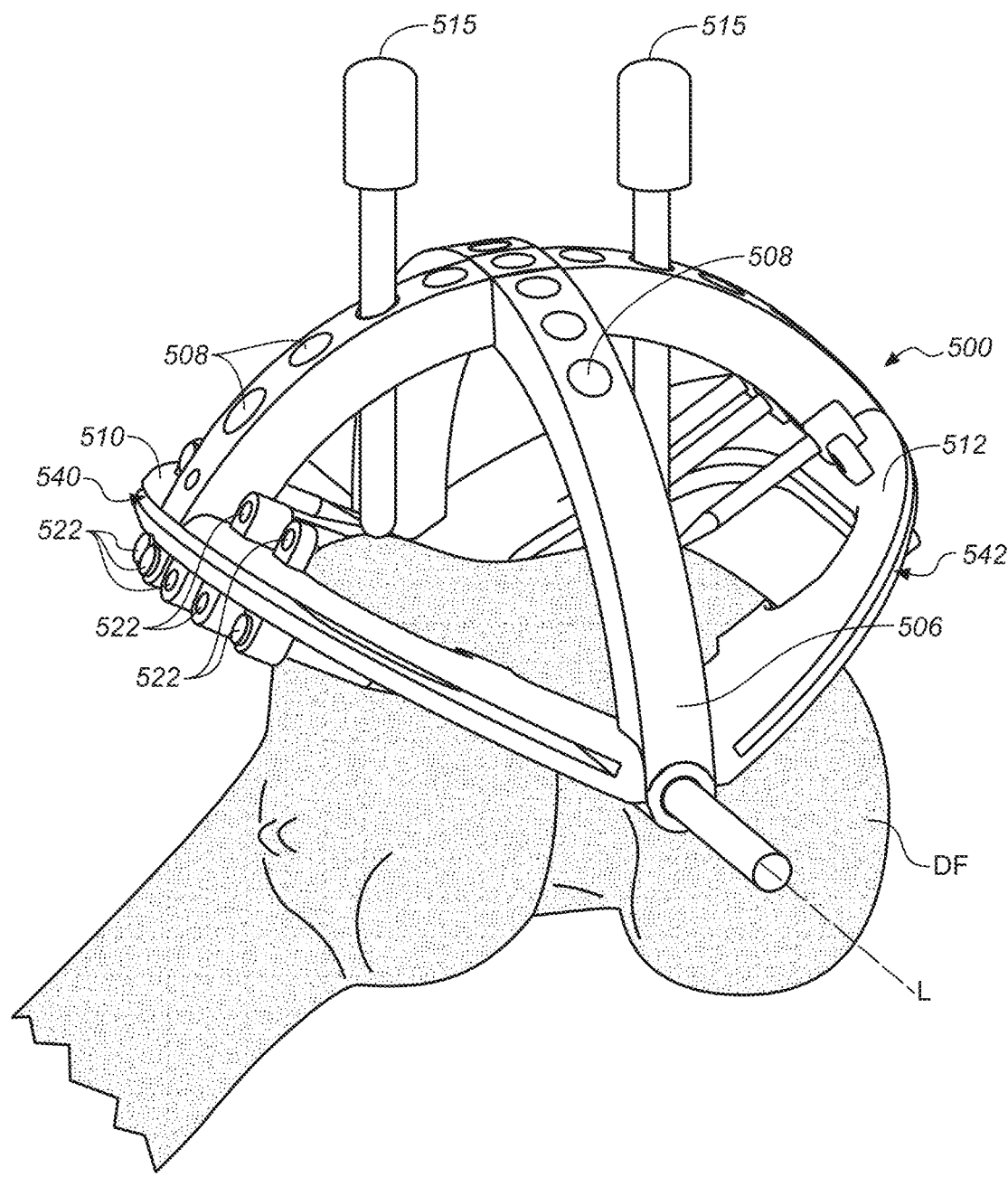
FIG. 51 is a distal perspective view of the diseased femur with the trochlear cutting guide installed on the abnormal dysplastic femur.
Figure 52:
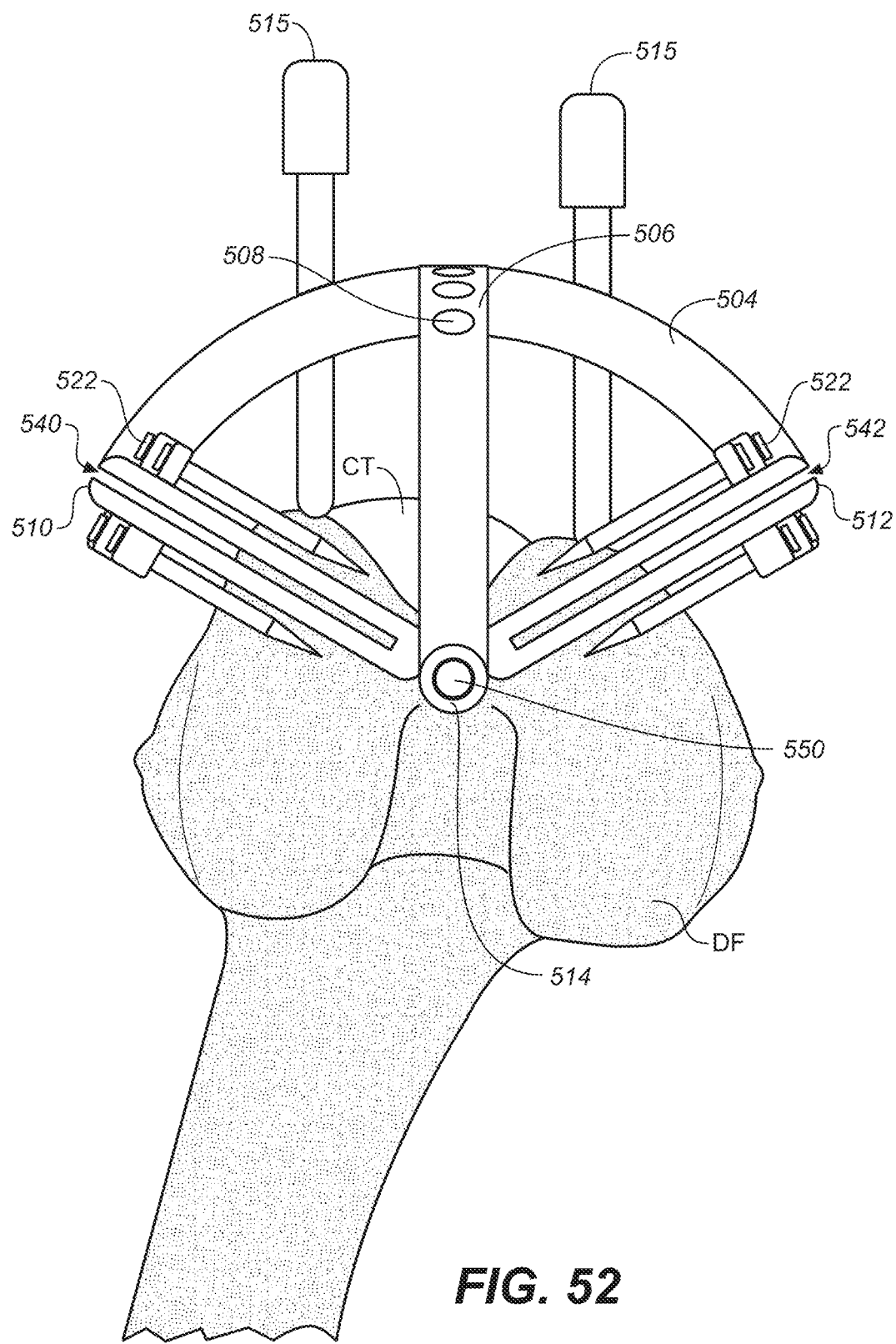
FIG. 52 is a distal view thereof slightly medial of the view of FIG. 51.
Figure 53:
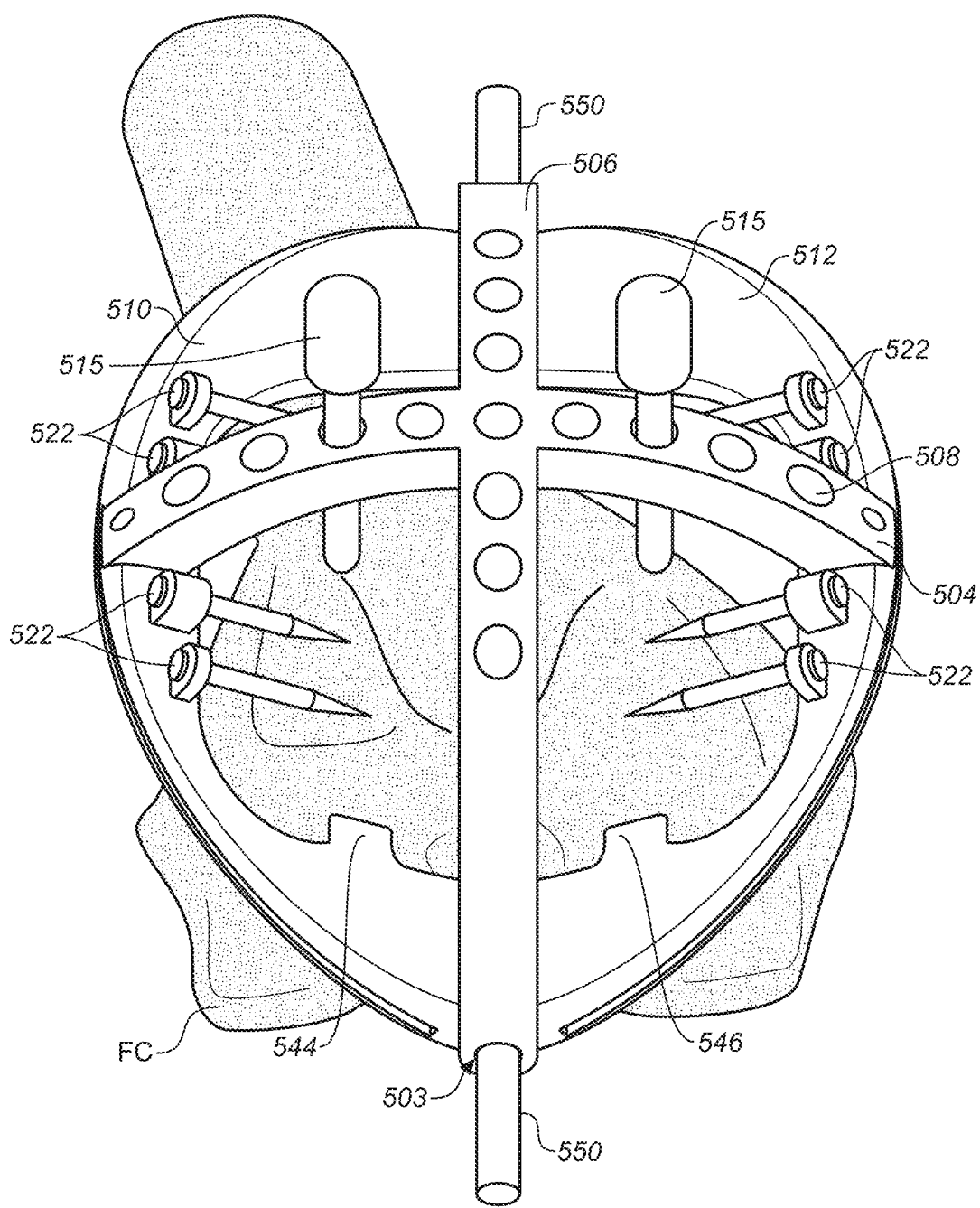
FIG. 53 is a superior view of the diseased femur with the trochlear cutting guide mounted on the abnormal dysplastic portion of the femur and showing multiple reference spacers but none referencing the dysplastic portion of the femoral trochlea.

FIGS. 51-53 are distal perspective, distal, and superior views, respectively, of the diseased femur DF with the trochlear cutting guide 500 is mounted on the abnormal, dysplastic femur. The reference spacers 515 disposed through the fixation holes 508 are shown with their proximal expansions 515b and distal rounded tips 515a placed within the guide to reference the surface of the diseased trochlea. Due to the misshapen trochlea, the pins that would make contact with the diseased portion are not filled, and only those that contact the morphologically normal part of the trochlea are used as reference guides. In particular, toward its peripheral edges the trochlea is normal and those reference spacers are used while more centrally they are not used. The spacers also allow the guide to be positioned in line with the sulcus of the trochlea in the coronal plane and to allow the optimal amount of bone to be removed to accommodate the healthy trochlea obtained previously from the graft. Two cutting elements 510, 512 are placed at the inferior aspect of the guide converging in a virtual line L. The cutting elements are disposed with fixation holes 522 for holding the guide against the native diseased femoral bone both above and below the cutting elements. The distal cylindrical hole 503 and proximal cylindrical hole 505 (not shown) are aligned for placement of the holding rod 550. The referencing platforms 544, 546 on the distal inner circumference are shown. These make contact with the articular cartilage surface of the relatively normal femoral condyles of the diseased knee in order to ensure that the graft previously obtained and the recipient site have an ideal surface match at their transition from the trochlea to the femoral condyles. The holding rod 550 is positioned directly on the line where the cutting planes of the cutting elements intersect.

Figure 54A:
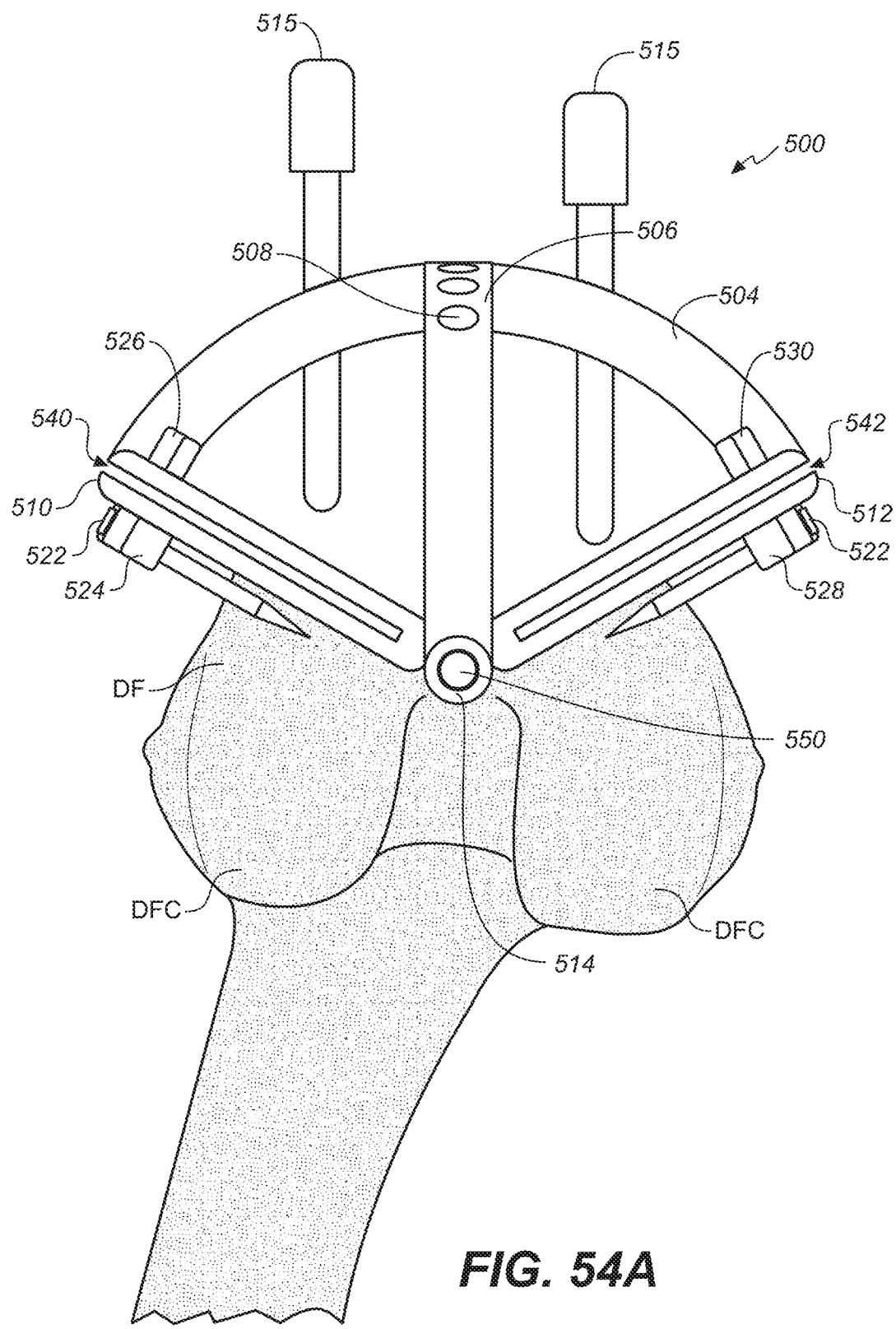
FIG. 54A is a distal view thereof showing the diseased femur after cutting and removal of the diseased, dysplastic segment, this view showing the cutting guide still installed on the bone.
Figure 54B:
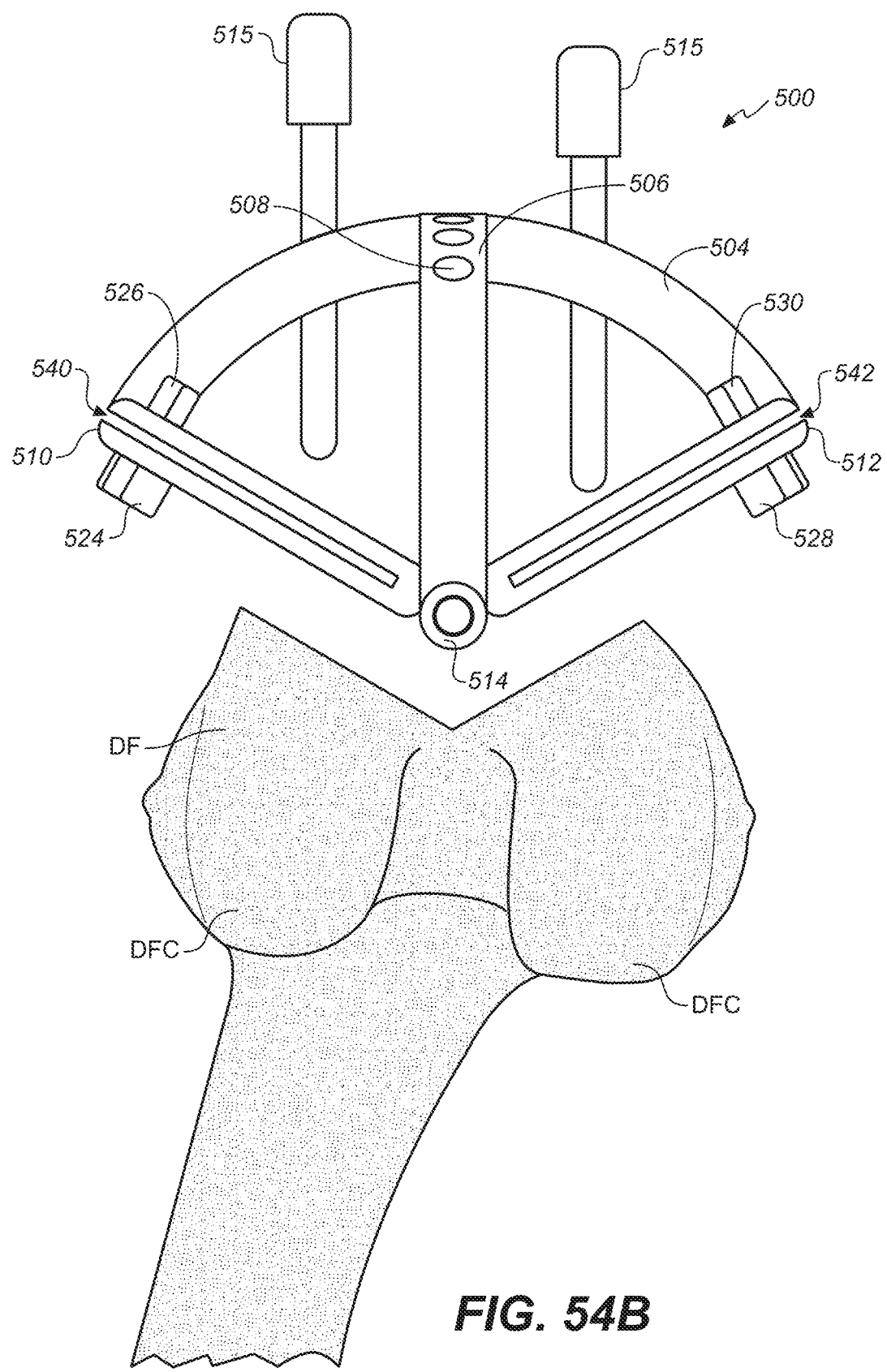
FIG. 54B is the same view showing the cutting guide removed from the bone.

FIGS. 54A and 54B are distal views of the diseased femur after removal of the diseased trochlea. The trochlear guide remains in place and is removed by removal of the pins passed through fixation holes 522 at the bottom surface of the cutting elements and by removal of the holding rod 550 that had previously been passed from the distal cylindrical hole 503 through the trochlea (not visible in this view). The distal femoral condyles DFC of the patient's femur are not affected.

Figure 55:
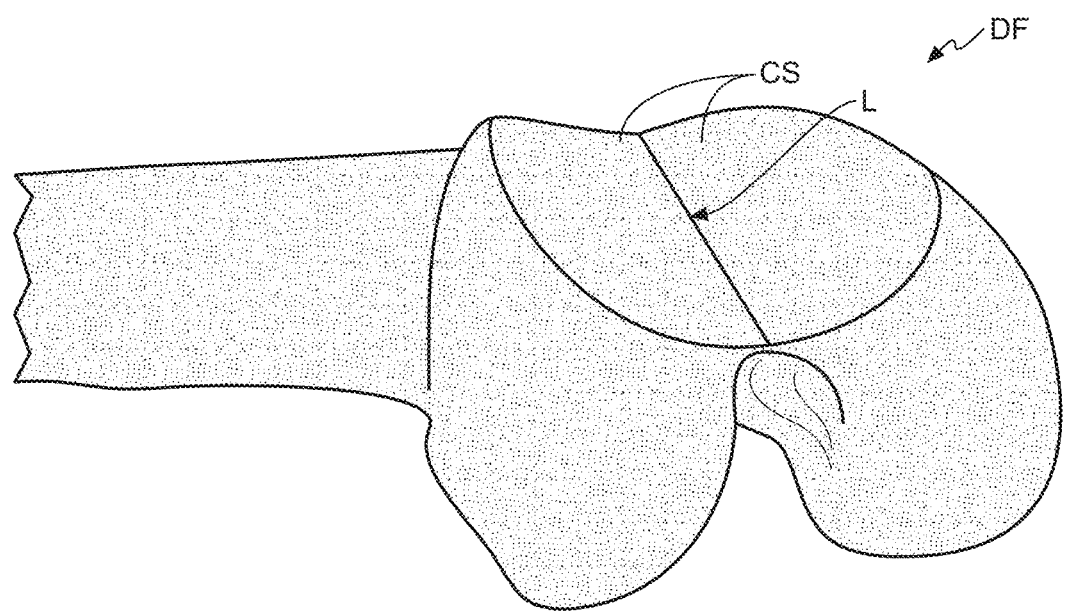
FIG. 55 is a distal perspective view of the diseased femur after removal of the diseased, dysplastic trochlea and after removal of the trochlear guide.

FIG. 55 is a distal perspective view of the diseased femur DF after removal of the diseased trochlea and after removal of the trochlear guide. The cut surfaces CS converge at the line connected by the cutting slots 540, 542 (not shown) and by the holding rod 550 (not shown). The two cutting surfaces are at the same angle to one another as the particular guide used for the recovery. The healthy distal femoral condyles are untouched.

Figure 56:
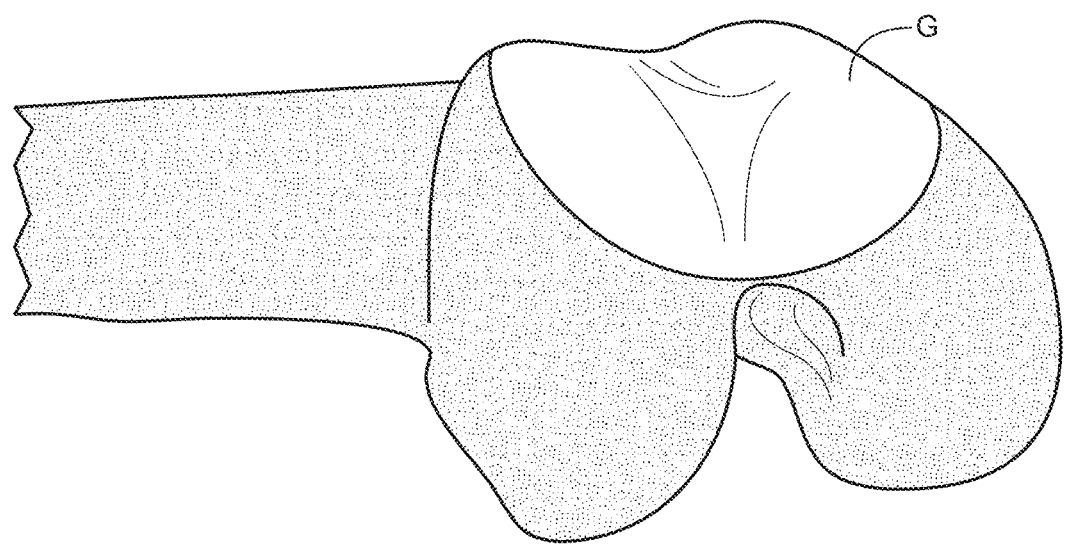
FIG. 56 is a distal perspective view of the diseased femur after placement of the previously obtained healthy and normally shaped allograft trochlea.

FIG. 56 is a distal perspective view of the diseased femur DF after placement of the previously obtained allograft trochlea onto the recipient site prepared using the same guide. By referencing the trochlear surface and the distal femoral condyles, a perfect match of the cartilage surfaces is achieved and a smooth transition between the trochlear graft and the patient's femoral condyles is achieved.

In the foregoing paragraphs, various preferred embodiments of the inventive bone cutting guide have been described in fulfillment of the various objects of the invention. It will be recognized by those with skill in the art that these embodiments are merely illustrative of the principles of the invention. Modifications and adaptations thereof will be apparent those skilled in the art without departing from the spirt and scope of the invention. The above-described surgical device and the techniques for using it can be applied to a wide variety of joints and are not limited to application in the human knee or hip. Therefore, the above description and illustrations should not be construed as limiting the scope of the invention, which is defined by the appended claims.

What is claimed as invention is:

1. An acetabular bone cutting guide assembly for preparing both donor and recipient bone, comprising:
    an articular referencing platform configured for placement on, and resurfacing of, at least the superior weight-bearing portion of the human acetabulum;
    wherein said referencing platform is part of a modular acetabular cutting tool and is shaped as a hemispherical body that precisely contacts the articular surface of the acetabulum;
    said hemispherical body having a lower circumferential rim;
    a fixation structure to secure said articular referencing platform on an articular surface;
    a first vertical cutting tower and a second vertical cutting tower spaced apart and extending from said hemispherical body radially to said lower circumferential rim;
    said first vertical cutting tower having a first vertically oriented cutting slot;
    said second vertical cutting tower having a second vertically oriented cutting slot;
    said first and said second vertically oriented cutting slots are formed in spaced apart said first and second vertical cutting towers, configured such that each said first and second vertically oriented cutting slots is aligned with respective first and second radially oriented cutting slots in said hemispherical body radial to said lower circumferential rim;
    an axial cutting tool disposed between said first and second vertically oriented cutting slots in respective first and second vertical cutting towers, said axial cutting tool and having a first axial cutting slot as a central cutting slot for placement of a saw to separate bone previously cut through respective said first and second vertically oriented cutting slots and respective said first and second radially oriented cutting slots; and
    said first and said second vertically oriented cutting slots and said first axial cutting slot spaced apart from said articular referencing platform at predetermined distances configured to allow the passage of a saw blade in such a way to remove a bone segment either from an allograft donor or from a graft recipient in such a way that both the removed donor and recipient grafts are of the same exact dimensions, whereby when the allograft is placed in the recipient site of the patient's joint, it completely restores the articular surface to the desired level with healthy articular cartilage from the donor.

2. The acetabular bone cutting guide assembly of claim 1, wherein said first and second radially oriented cutting slots are positioned proximate said lower circumferential rim of said hemispherical body at an angle of between 30 and 150 degrees to one another.

3. The acetabular bone cutting guide assembly of claim 1, further including guide pin holes disposed on each of said first and second vertical cutting towers proximate said first and second vertical cutting slots, respectively, for placement of guide pins to stabilize said bone cutting guide assembly to an acetabular bone, and configured so as to prevent a reciprocating saw disposed through said first or second vertical cutting slot from cutting respective guide pins disposed through said guide pin holes.

4. The acetabular bone cutting guide assembly of claim 3, wherein said axial cutting tool is an arcuate bar removably mounted on said first and second vertical cutting towers.

5. The acetabular bone cutting guide assembly of claim 4, wherein said arcuate bar includes a plurality of bosses with through holes for placement of fixation pins.

6. The acetabular bone cutting guide assembly of claim 1, wherein said first and second vertical cutting towers are disposed at an angle of between 30 and 150 degrees relative to one another.

7. The acetabular bone cutting guide assembly of claim 6, wherein said axial cutting tool further includes an arcuate bar.

* * * * *